United States Patent

Brojatsch et al.

[11] Patent Number: 5,912,141
[45] Date of Patent: Jun. 15, 1999

[54] NUCLEIC ACIDS ENCODING TUMOR VIRUS SUSCEPTIBILITY GENES

[75] Inventors: Jürgen Brojatsch, Jamaica Pond; John Naughton, Somerville; John A. T. Young, Auburndale, all of Mass.

[73] Assignee: President & Fellows of Harvard College, Cambridge, Mass.

[21] Appl. No.: 08/651,579

[22] Filed: May 22, 1996

[51] Int. Cl.[6] .................. C12N 15/10; C12N 15/12; C12N 5/10; C07K 14/705
[52] U.S. Cl. .................. 435/69.1; 530/350; 530/300; 530/826; 536/23.1; 536/23.4; 536/23.5; 435/69.7; 435/320.1; 435/325; 435/252.3; 435/254.11
[58] Field of Search .................. 536/23.5, 23.1, 536/23.4; 530/350, 826, 300; 435/69.1, 6, 69.7, 320.1, 325, 252.3, 254.11

[56] References Cited

U.S. PATENT DOCUMENTS 5,395,760   3/1995   Smith et al. .................. 435/240.1

OTHER PUBLICATIONS

George, et al. in Macromolecular Sequencing and Synthesis: Selected Methods and Applications (Schlesinger, D. ed), pp. 127–149, Alan R. Liss, Inc., New York, NY, 1988.

Brojatsch, J. et al. (1996) "CAR1, a TNFR–related protein, is a cellular receptor for cytopathic avian Leukosis–Sarcoma viruses and mediates apoptosis" *Cell*, 87:845–855.

Suter, B. et al. (1995) "Cloning of the cDNA encoding the porcupine p55 tumor necrosis factor receptor" *Gene*, 163(2):263–266.

Weiss, R.A. et al. (1995) "Retrovirus receptors" *Cell*, 82:531–533.

Johnson, E., "Poultry Oncogenic Retroviruses and Humans," *Cancer Detection and Prevention*, vol. 18, No. 1, 9–30 (1994).

Nagata, S. and Golstein, P., "The Fas Death Factor," *Science*, vol. 267, 1449–56 (1995).

Owen–Schaub, L. et al., "Soluble Fas/APO–1 in Tumor Cells: a Potential Regulator of Apoptosis;" *Cancer Letters*, vol. 94, 1–8 (1995).

(List continued on next page.)

*Primary Examiner*—Lila Feisee
*Assistant Examiner*—Claire M. Kaufman
*Attorney, Agent, or Firm*—Giulio A. DeConti, Jr.; Lahive & Cockfield, LLP

[57] ABSTRACT

The present invention concerns the discovery of a new member of the TNF receptor superfamily, referred to herein as the candidate "tvb receptor". Experimental evidence suggests that the instant gene corresponds to the gene of the $tvb^{s3}$ locus responsible for mediating certain viral infection. The tvb receptor plays a functional role as the receptor for certain of the avian leukosis/sarcoma viruses (ALSV) in avians, and a likely role as a receptor for tumor viruses in other animals, e.g., the feline leukemia virus and the like. Moreover, inspection of the tvb sequence, particularly in comparison with other TNF receptors, reveals the presence of a "death domain" in the cytoplasmic tail of the tvb receptor, suggesting a role for the tvb receptor in determining tissue fate and maintenance. For instance, the tvb genes and gene products may participate, under various circumstances, in the control of proliferation, differentiation and/or cell death.

17 Claims, 5 Drawing Sheets

OTHER PUBLICATIONS

Tartaglia, L. et al., A Novel Domain Within the 55 kd TNF Receptor Signals Cell Death, *Cell,* vol. 74, 845–53 (1993).

Vogt, P. and Ishizaki, R., "Reciprocal Patterns of Genetic Resistance to Avian Tumor Viruses in Two Lines of Chickens," *Virology,* vol. 26, 664–72 (1965).

Weller, S. and Temin, H., "Cell Killing by Avian Leukosis Viruses," *Journal of Virology,* vol. 39, No. 3, 713–21 (1981).

Weller, S. et al., "Correlation Between Cell Killing and Massive Second–Round Superinfection by Members of Some Subgroups of Avian Leukosis Virus," *Journal of Virology,* vol. 33, No. 1, 494–506 (1980).

Wiegmann, K. et al., "Human 55–kDa Receptor for Tumor Necrosis Factor Coupled to Signal Transduction Cascades," *The Journal of Biological Chemistry,* vol. 267, No. 25, 17997–18001 (1992).

Young, J. et al., "Isolation of a Chicken Gene that Confers Susceptibility to Infection by Subgroup A Avian Leukosis and Sarcoma Viruses," *Journal of Virology,* vol. 67, No. 4, 1811–6 (1993).

Armitage, R., "Tumor Necrosis Factor Receptor Superfamily Members and Their Ligands," *Current Opinion in Immunology,* vol. 6, 407–13 (1994).

Baker, S. and Reddy, E., "Transducers of Life and Death: TNF Receptor Superfamily and Associated Proteins," *Oncogene,* vol. 12, 1–9 (1996).

Banner, D. et al., "Crystal Structure of the Soluble Human 55 kd TNF Receptor–Human TNFβ Complex: Implications for TNF Receptor Activation," *Cell,* vol. 73, 431–45 (1993).

Bates, P. et al., "A Receptor for Subgroup A Rous Sarcoma Virus is Related to the Low Density Lipoprotein Receptor," *Cell,* vol. 74, 1043–51 (1993).

Beutler B. and Van Huffle, C., "An Evolutionary and Functional Approach to the TNF Receptor/Ligand Family," *Annals New York Academy of Sciences,* vol. 730, 118–133 (1994).

Bova, C. et al., "env Genes of Avian Retroviruses: Nucleotide Sequence and Molecular Recombinants Define Host Range Determinants," *Virology,* vol. 152, 343–54 (1986).

Cleveland, J. and Ihle, J., "Contenders in FasL/TNF Death Signaling," *Cell,* vol. 81, 479–82 (1995).

Crittenden, L. et al., "Two Loci Controlling Genetic Cellular Resistance to Avian Leukosis–Sarcoma Viruses," *Journal of Virology,* vol. 1, No. 5, 898–904 (1967).

Diez–Ruiz, A. et al., "Soluble Receptors for Tumour Necrosis Factor in Clinical Laboratory Diagnosis," *Eur J Haematol,* vol. 54, 1–8 (1995).

Dorner, A. and Coffin, J., "Determinants for Receptor Interaction and Cell Killing on the Avian Retrovirus Glycoprotein gp85," *Cell,* vol. 45, 365–74 (1986).

Gilbert, J. et al., "The Receptor for the Subgroup A Avian Leukosis–Sarcoma Viruses Binds to Subgroup A but not to Subgroup C Envelope Glycoprotein," *Journal of Virology,* vol. 68, No. 9, 5623–8 (1994).

Gruss, H. and Dower, S., "Tumor Necrosis Factor Ligand Superfamily: Involvement in the Pathology of Malignant Lymphomas," *Blood,* vol. 85, No. 12, 3378–3404 (1995).

The Putative Tvb Protein Contains a Cytoplasmic Region with Similarity to the "Death Domains" of Fas and TNRR

```
                                            *                    *                          *
V D Y - V P F P E W K R F G R A L D L Q E N D L Y L A E Q H D R V S C E P F Y - Q    Put. Tvb    SEQ ID NO:16
V V E N V P L R W K E F V R R L G L S D H E H D R L Q N G R - C L R E A - Q          p55-hTNFR   SEQ ID NO:17
I A G V M T L S Q V K K G F V R K N G V N E A K I D E I K N D N V Q D T A E Q K V Q  hFas        SEQ ID NO:18
                    *           *                 lpr
                                                   *

*                                     *
- M L N T W L N Q Q G S K A S V N T L L E - T L P R I G L - S G V A D I H A S        Put. Tvb
Y S M L A T W R R T P R R E A T L E L L G R V L R D M D L - L G C L E D I E E        p55-hTNFR
- - L L R N W H - Q L H G K K E A Y D T L I K D L K K A N L C T L A - E K I H Q T    hFas
```

Fig. 3

A cDNA Clone that Confers Susceptibility to Subgroup B and D ALSV Infection

| Viral Subgroup | COS-7 | Transfected COS-7 (Put. Tvb+) |
|---|---|---|
| A | 0 | 1 |
| B | 0 | 7,000 |
| C | 5 | 7 |
| D | 780 | 8,000 |

G418-Resistant Colonies/ml Virus

Fig. 5

```
SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 2413 base pairs
         (B) TYPE: nucleic acid
         (C) STRANDEDNESS: both
         (D) TOPOLOGY: linear (ii) MOLECULE TYPE: cDNA (ix) FEATURE:
         (A) NAME/KEY: CDS
         (B) LOCATION: 215..1318

(xi) SEQUENCE DESCRIPTION: SEQ ID NO:1:

GGGTTGTTGG TAGGGGGGTA CTAAAGGGAA CAAAAGCTGA AACAGCTATA CCTTATTACG         60

CCAAGCTCGA ATAAACCCTC ACTAAAGGGA ACAAAAGCTG GAGCTCGCGG CCTGCAGGTC        120

GACACTAGTG GATCCAAAGA ATTCGGCACG AGGTTCCTAA CTCGGTCCGA ATCCGGATCT        180

CAGCCCGGGC GCAGCGCGCT CCGCTCCGCG CACG ATG CGC TCA GCT GCG CTC            232
                                      Met Arg Ser Ala Ala Leu
                                       1               5

CGG TTG TGC CCC GTT CTA CTG CTG CTC TTC GCG GAG GTT CAG TTG GGA          280
Arg Leu Cys Pro Val Leu Leu Leu Leu Phe Ala Glu Val Gln Leu Gly
         10                  15                  20

TCT GCT GCA GCA GTG AAG AAG AGG GCA GAC AGG TCA GAC CTC CAG AAG          328
Ser Ala Ala Ala Val Lys Lys Arg Ala Asp Arg Ser Asp Leu Gln Lys
     25                  30                  35

CCA GAC CTC TAC AGA AGG AAG TGT CCT ATG GGC ACC TAT GAG GCA AAT          376
Pro Asp Leu Tyr Arg Arg Lys Cys Pro Met Gly Thr Tyr Glu Ala Asn
```

-continued

```
            40                  45                  50
GAC TCC ATC CAG TGC CTC CCA AGT AAG AAA GAC GAG TAC ACC GAG TAT      424
Asp Ser Ile Gln Cys Leu Pro Ser Lys Lys Asp Glu Tyr Thr Glu Tyr
 55                  60                  65                  70

CCA AAT GAC TTT CCC AAG TGC CTG GGC TGC CGG ACG TGT AGG GAA GAC      472
Pro Asn Asp Phe Pro Lys Cys Leu Gly Cys Arg Thr Cys Arg Glu Asp
             75                  80                  85

CAG GTG GAG GTG AGT CCC TGC ATC CCC ACC AGG AAC ACG CAG TGC GCT      520
Gln Val Glu Val Ser Pro Cys Ile Pro Thr Arg Asn Thr Gln Cys Ala
                 90                  95                 100

TGC AAG AAC GGC ACC TTC TGC TTA CCT GAC CAC CCC TGT GAG ATG TGC      568
Cys Lys Asn Gly Thr Phe Cys Leu Pro Asp His Pro Cys Glu Met Cys
            105                 110                 115

CAA AAG TGC CAG ACC GAG TGC CCC AAA GGA CAA GTG AGG TTA GCT CCG      616
Gln Lys Cys Gln Thr Glu Cys Pro Lys Gly Gln Val Arg Leu Ala Pro
120                 125                 130

TGC ACG CAA CAC AGC GAC CTG CTG TGC GGT CCA CCC TTG GAA ATC TCC      664
Cys Thr Gln His Ser Asp Leu Leu Cys Gly Pro Pro Leu Glu Ile Ser
135                 140                 145                 150

TCC AGC TCC TCC ACT TTA TGG ATC ATC ATC ACC TTC ACC GTG CTG CTG      712
Ser Ser Ser Ser Thr Leu Trp Ile Ile Ile Thr Phe Thr Val Leu Leu
                155                 160                 165

GCT GTG ATC CTG GGG CTC GTG CTG GTG TTC TGG AAG AGG TGC TCC TCC      760
Ala Val Ile Leu Gly Leu Val Leu Val Phe Trp Lys Arg Cys Ser Ser
            170                 175                 180

AGA CAC CAC GGT GCA GGG GAT GAT GGA GAG CTG AGC TGG AAG CCC AGC      808
Arg His His Gly Ala Gly Asp Asp Gly Glu Leu Ser Trp Lys Pro Ser
            185                 190                 195

GCC GTG GTG AAC AGA CTG TTG CAG CGG CTG GGG ATT CAG GAC AAC AGA      856
Ala Val Val Asn Arg Leu Leu Gln Arg Leu Gly Ile Gln Asp Asn Arg
    200                 205                 210

TGC AAT GAG CAG ATC TAC CAG AAC CAG CAG CAG GAG CTG CTT TTC          904
Cys Asn Glu Gln Ile Tyr Gln Asn Gln Gln Gln Glu Leu Leu Phe
215                 220                 225                 230

ACA GCG CAG GGC TCA GAG GTT CCC CAT GGT GTG GAG ATG GAG GGG ACG      952
Thr Ala Gln Gly Ser Glu Val Pro His Gly Val Glu Met Glu Gly Thr
                235                 240                 245

GAA CGA AGA ACC CCA GAT CCC AAA GTG GAA ACC CAG AGG AAG CTG GTT     1000
Glu Arg Arg Thr Pro Asp Pro Lys Val Glu Thr Gln Arg Lys Leu Val
            250                 255                 260

CCA GTG CTA GGA GAG AAC CCC ATA GCC CTT TTG CAT CGC TCT TTC AAC     1048
Pro Val Leu Gly Glu Asn Pro Ile Ala Leu Leu His Arg Ser Phe Asn
            265                 270                 275

ACC TTT GTC GAC TAT GTG CCC TTC CCG GAA TGG AAG AGA TTT GGC CGA     1096
Thr Phe Val Asp Tyr Val Pro Phe Pro Glu Trp Lys Arg Phe Gly Arg
    280                 285                 290

GCC CTC GAC CTG CAG GAA AAC GAC CTT TAT CTG GCA GAG CAG CAC GAC     1144
Ala Leu Asp Leu Gln Glu Asn Asp Leu Tyr Leu Ala Glu Gln His Asp
295                 300                 305                 310

AGG GTC TCA TGT GAG CCG TTC TAT CAG ATG CTC AAC ACG TGG CTC AAC     1192
Arg Val Ser Cys Glu Pro Phe Tyr Gln Met Leu Asn Thr Trp Leu Asn
                315                 320                 325

CAA CAG GGC AGC AAA GCC TCT GTG AAT ACG CTG CTG GAG ACC CTG CCC     1240
Gln Gln Gly Ser Lys Ala Ser Val Asn Thr Leu Leu Glu Thr Leu Pro
            330                 335                 340

CGC ATC GGC CTC AGC GGC GTG GCA GAC ATA ATT GCA TCC GAA CTC ATT     1288
Arg Ile Gly Leu Ser Gly Val Ala Asp Ile Ile Ala Ser Glu Leu Ile
            345                 350                 355

AGC AAG GGC TAT TTC CAG TAC GAG GTG AGC TGAGGGGCAC GGCCAGCCCC       1338
Ser Lys Gly Tyr Phe Gln Tyr Glu Val Ser
```

-continued

```
             360         365
GCGTCTCCCC GGCTGGAGCT GAAGATGTGA ATTCCTTTGA GAACCCTTAT CTTGATCTCT    1398

GTGACAGTGC TCTCGTGGCT CCTTTCTCCC TGAGCCATCG CACAGTTCAG CTGAGCCTGG    1458

AGGAGTGGAT CCCATTGGGA AGCAATTGGG GTCTTCTCTG CCACACTCAG CGTTGGTGCT    1518

GCCTTATGGA AGCCAAGCGA GTGCCTTGAT TTCATCTGGC AACGCAATG  AGCCAAAAGG    1578

TCTTCCAAAC TGCCTTTGAG ATCATCTGAT TTGCAAGCAC TGATTTCATA CAGACCTCGG    1638

TGCAGAGCTG CACCTTTGCT TGGTGCAGGC ACTCACTGGT TCGAACTGGA TCCACGTTTT    1698

GAAGCTTTTT ATTACTTTTT TTTAGTGATA TTTCTGCTTG TAGAACATCT CCGAGCGCAC    1758

CGTCATGCTT AGCACTGCAT GCCTGGTGGG CGAGCATCTC TGGGACTCCT GGGTTACCCC    1818

CTACAGTCTA TTTAGAGTTG CATTCGTAGC TAGTTCTGCT TGCCCTTAGG AGTAGACACA    1878

AGAGTATAGC AGTGGGGTTG GTGATCTCCA AGGTCCCTTC CAACCCAAGC CCACCATTGT    1938

ACGACTGTAG GCGATGCGGG CGCGATCCAT CGGCGCGAGG CTGCCCTAAT AGGGCTGGTG    1998

GAGGCTGGGT CGGTTCATTC CCATTGCCAG GGCTCCTCCA CCTCCAGGGA CAGCACACAG    2058

CTCAGGGATG AGGTGTTGCA GCCCTCCTGC ACGCCTTGGC TGGGTGATGG TGCTGCAGTC    2118

CAACCCCGGG AGCTCCCCTG TGCGGGGCAG GGTTGTGGGG AGCCCCTCTG CACCCCTCTC    2178

CGTCCTCTCC ACCCCTGTGC CAAATACCAG CAGAACTTTT GTATTTATGT ATTTATTAAT    2238

TGTAAACACG TACATTGCAT TAACTTAAAA TATAATATAA AAATAAAAAA AAAAAAAAA     2298

AAAACTCGAG AGTACTTCTA GAGCGGCGCG GGCCCATCGA TTTTCCACCC GGGTGGGGTA    2358

CCAGGTAAGT GTACCCAATT CGCCCTATAG TGAGTCGTAT TACAATTCAC TGGCC         2413
```

(2) INFORMATION FOR SEQ ID NO:2:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Ser Ala Ala Leu Arg Leu Cys Pro Val Leu Leu Leu Phe
 1               5                  10                  15

Ala Glu Val Gln Leu Gly Ser Ala Ala Val Lys Lys Arg Ala Asp
                20                  25                  30

Arg Ser Asp Leu Gln Lys Pro Asp Leu Tyr Arg Arg Lys Cys Pro Met
        35                  40                  45

Gly Thr Tyr Glu Ala Asn Asp Ser Ile Gln Cys Leu Pro Ser Lys Lys
     50                  55                  60

Asp Glu Tyr Thr Glu Tyr Pro Asn Asp Phe Pro Lys Cys Leu Gly Cys
 65                  70                  75                  80

Arg Thr Cys Arg Glu Asp Gln Val Glu Val Ser Pro Cys Ile Pro Thr
                85                  90                  95

Arg Asn Thr Gln Cys Ala Cys Lys Asn Gly Thr Phe Cys Leu Pro Asp
            100                 105                 110

His Pro Cys Glu Met Cys Gln Lys Cys Gln Thr Glu Cys Pro Lys Gly
        115                 120                 125

Gln Val Arg Leu Ala Pro Cys Thr Gln His Ser Asp Leu Leu Cys Gly
    130                 135                 140

Pro Pro Leu Glu Ile Ser Ser Ser Ser Thr Leu Trp Ile Ile Ile
145                 150                 155                 160
```

-continued

```
Thr Phe Thr Val Leu Leu Ala Val Ile Leu Gly Leu Val Leu Val Phe
            165             170             175

Trp Lys Arg Cys Ser Ser Arg His His Gly Ala Gly Asp Asp Gly Glu
            180             185             190

Leu Ser Trp Lys Pro Ser Ala Val Val Asn Arg Leu Leu Gln Arg Leu
            195             200             205

Gly Ile Gln Asp Asn Arg Cys Asn Glu Gln Ile Tyr Gln Asn Gln Gln
    210             215             220

Gln Gln Glu Leu Leu Phe Thr Ala Gln Gly Ser Glu Val Pro His Gly
225             230             235             240

Val Glu Met Glu Gly Thr Glu Arg Arg Thr Pro Asp Pro Lys Val Glu
            245             250             255

Thr Gln Arg Lys Leu Val Pro Val Leu Gly Glu Asn Pro Ile Ala Leu
            260             265             270

Leu His Arg Ser Phe Asn Thr Phe Val Asp Tyr Val Pro Phe Pro Glu
            275             280             285

Trp Lys Arg Phe Gly Arg Ala Leu Asp Leu Gln Glu Asn Asp Leu Tyr
    290             295             300

Leu Ala Glu Gln His Asp Arg Val Ser Cys Glu Pro Phe Tyr Gln Met
305             310             315             320

Leu Asn Thr Trp Leu Asn Gln Gln Gly Ser Lys Ala Ser Val Asn Thr
            325             330             335

Leu Leu Glu Thr Leu Pro Arg Ile Gly Leu Ser Gly Val Ala Asp Ile
            340             345             350

Ile Ala Ser Glu Leu Ile Ser Lys Gly Tyr Phe Gln Tyr Glu Val Ser
            355             360             365
```

NUCLEIC ACIDS ENCODING TUMOR VIRUS SUSCEPTIBILITY GENES

BACKGROUND OF THE INVENTION

Since the initial identification of TNF-α and TNF-β, these proteins have become representative of a unique superfamily of ligands which currently includes TNF-α, TNF-β, Fas ligand (L), OX40L, CD40L, CD27L, CD30L, 4-1BBL and LTβ (Baker et al. (1996) *Oncogene* 12:1–9). Each of the ligands is a type II membrane protein which is characterized by the confinement of the C-terminus of the protein within the extracellular space. A 150 amino acid region within the C-terminus is actually the hallmark of the ligand family, as this is the region which the ligands bind to their cognate receptors. In contrast to other protein families with notable homology, each of these family members displays no more than 20–25% homology (which is found mostly in the extracellular region) at the protein level. Although these proteins, for the most part, exist as multimeric membrane bound proteins which function to induce receptor aggregation, there are a few members, such as TNF-α and FasL, which are functional in a soluble form. Regardless of conformation, these ligands, in a mechanism analogous to other cytokines and growth factors, exert their effects through receptor-ligand interactions which induce downstream signal transduction events.

There are slightly more members of the TNF receptor (TNFR) superfamily as there are known ligands with which they interact: TNF-RI (p55), TNF-RII(p75), TNF-RIII (TNF-RP), OX-40, 4-1BB, CD40, CD30, CD27, the poxvirus gene products PV-T2 and PV-A53R, and p75 BGFR. The mammalian TNFR family members are type I membrane proteins and, in spite of their low degree of homology (20–25%), are grouped together as such due to the presence of conserved cysteine residues in the extracellular ligand-binding domain. In general, each receptor contains varying numbers of cysteine-rich domains (CRDs), each of which is characterized by the presence of approximately 6 cysteine residues that are interspersed within a stretch of 40 amino acids. The presence of the CRDs, based on available crystallographic data for TNF-RI, has allowed this protein superfamily to add a different perspective from which these (as opposed to other) growth factor receptors are studied: a functional TNF superfamily is typically a trimeric or multimeric complex which is stabilized via intracysteine disulfide bonds that are formed between the CRDs of individual subunit members (Banner et al. (1993) *Cell* 73:431–445). Despite an emphasis on the CRDs and the formation of membrane bound aggregated complexes, most receptors also exist in a soluble form. Solubility is, for the most part, achieved by proteolytic cleavage and soluble forms of TNF-RI, TNF-RII, CD27, CD30, CD40 and Fas are generated in this fashion; while 4-1BB also exists in a soluble form, it is generated via alternate splicing (Gruss et al. (1995) *Blood* 85:3378–3404).

Irrespective of ligand and receptor conformation, both TNF-related ligands and receptors are expressed on (but necessarily limited to) activated T cells and are, in one form or another, required during T cell mediated immune responses. This type of coordinated expression and function is thought to ensure that such responses, which are largely dependent upon antigen stimulation and subsequent cell-cell interactions, are initiated at the proper times, in the appropriate places, and involve the correct cell types (each of which will express either the ligand or the receptor). Frequently the outcome of such cellular responses can be quite pleiotropic, generating a broad range of cellular responses in the forms of T-cell activation and death, cellular proliferation and differentiation, or cell death which proceeds via apoptosis (Armitage (1994) *Cur Opin Immunol* 6:406–413; Gruss et al., supra).

Sequence and functional analysis of the various TNF receptor members has revealed a conserved region occurring in the cytoplasmic tail of the Fas and TNF-RI receptors. The term "death domain" was originally coined in 1993 by Tartaglia et al. (Tartaglia L. A. et al., (1993) *Cell* 74:845–853) as a result of deletion mutagenesis studies involving TNF-RI (p55) mediated apoptotic cell death. These studies revealed that an 80 amino acid domain, which is localized to the C-terminal portion of the protein's intracellular region, is responsible for the generation of cytotoxic death signals, anti-viral responses (Tartaglia et al., supra), and the activation of acid sphingomyelinase (Wiegmann K. et al., (1994) *Cell* 78:1005–1015); it is also partially responsible for, in conjunction with residues in the N-terminal portion in the intracellular region, the induction of nitric oxide (NO) synthase activity (Tartaglia et al., supra). Homology searches have revealed that the TNF-RI death domain is approximately 65% similar (28% identical) to a 65 amino acid region within the intracellular domain of the Fas antigen; mutagenesis studies have confirmed that these 65 amino acids are required for the induction of cell death following treatment with an anti-Fas antibody in conjunction with actinomycin D (Itoh et al. (1993) *J. Biol. Chem.* 268:10932–10937). Supporting evidence for a functional overlap between the domains of these two receptors was achieved through the generation of a "death signal delivering" chimeric receptor which replaced TNF-RI amino acid residues 324–326 with the corresponding amino acids of the Fas antigen (Tartaglia et al., supra).

The death domain, aside from being the only homologous intracellular domain that is shared by two members of the TNFR superfamily, generates a cytotoxic signal irrespective of its position with respect to the extracellular domain (Tartaglia et al., supra). In addition, this domain appears to mediate self-association of both TNF-RI and Fas, thereby mimicking the aggregation of events which are induced by ligand binding to each of these receptors (Boldin M. P. et al., (1995) *J. Biol. Chem.* 270:387–391). These results, which demonstrate that the death domain is an independent domain at both the structural and functional levels, were recently confirmed by the identification and subsequent characterization of three death domain-containing proteins, each of which can generate an apoptotic signal when overexpressed in cells.

The rapid induction of cell death via the death domain is heretofore unique to TNF-RI and Fas; however, despite the characterization of a defined "death inducing" region within each of these receptors, the intermediates involved in the transmission of their signals were, until recently, completely unknown. As with other receptors which are devoid of catalytic activity, TNF-RI and Fas were suspected to utilize cellular protein as "downstream messengers of death." Many charged residues that are well conserved in both proteins were suspected to be widely dispersed throughout portions of the death domains which are oriented to interact with protein components of the cytoplasm (Tartaglia et al., supra). To date, three death domain-containing proteins which associate with either TNF-RI or Fas have been identified and characterized with respect to their ability to induce apoptosis and other downstream signaling events which are activated in immune responses achieved through ligand binding to each of these receptors.

The biologic role of the death domain of TNF-RI and Fas in apoptosis suggests that they may function as tumor supressors. For example, inactivation of Fas signaling as a consequence of loss of Fas/Fas ligand expression/function may lead to abnormal cellular survival and contribute to the development or progression of malignancy as a result of the failure to undergo apoptosis.

SUMMARY OF THE INVENTION

The present invention relates to the discovery of a new member of the TNF receptor superfamily, referred to herein as the candidate "tvb receptor," wherein "tvb" stands for the chicken autosomal locus governing tumor virus susceptibility in the series tva, tvb, and tvc.

In general, the invention features isolated tvb polypeptides, preferably substantially pure preparations of the subject tvb polypeptides. The invention also provides recombinantly produced tvb polypeptides. In preferred embodiments the polypeptide has a biological activity including one or more of: an ability to bind protein ligands of the TNF superfamily; an ability to transduce intracellular signals in response to binding ligands of the TNF superfamily, e.g., other than TNFα or Fas ligand; the ability to induce apoptosis; the ability to bind to virus, e.g., an avian leukosis/sarcoma virus or other tumor virus. However, tvb polypeptides which specifically antagonize such activities, such as may be provided by truncation mutants or other dominant negative mutants, are also specifically contemplated.

The tvb proteins of the present invention can be characterized as including one or more of the following domains/motifs: an extracellular domain having two cysteine rich domains which mediate ligand binding, a transmembrane domain, and an intracellular domain including a death domain. The protein may also include a secretion signal sequence, and/or glycosylated amino acid residues.

In one embodiment, the polypeptide is identical with or homologous to a tvb protein represented in SEQ ID No. 2. Related members of the tvb family are also contemplated, for instance, a tvb polypeptide preferably has an amino acid sequence at least 65%, 70%, 75% or 80% homologous to the polypeptide represented by SEQ ID No. 2, though polypeptides with higher sequence homologies of, for example, 85, 90% and 95% or are also contemplated. In a preferred embodiment, the tvb polypeptide is encoded by a nucleic acid which hybridizes under stringent conditions with a nucleic acid sequence represented in SEQ ID No. 1. Homologs of the subject tvb proteins also include versions of the protein which are resistant to post-translation modification, as for example, due to mutations which alter modification sites (such as tyrosine, threonine, serine or aspargine residues), or which prevent glycosylation of the protein, or which prevent interaction of the protein with TRAFs and/or other intracellular proteins involved in signal transduction.

The tvb polypeptide can comprise a full length protein, such as represented in SEQ ID No. 2, or it can comprise a fragment corresponding to one or more particular motifs/domains, or to arbitrary sizes, e.g., at least 5, 10, 25, 50, 100, 150 or 200 amino acids in length. In preferred embodiments, the tvb polypeptide includes a sufficient portion of the extracellular domain to be able to specifically bind to a ligand of the TNF superfamily. In other preferred embodiments, the tvb polypeptide includes a sufficient portion of the cytoplasmic domain to induce apoptosis, e.g., the polypeptide includes a death domain. Truncated forms of the protein include, but are not limited to, soluble extracellular domain fragments including one or both of the CRDs, soluble intracellular domains including the death domain, and membrane-bound forms of either which include the transmembrane domain.

In certain preferred embodiments, the invention features a purified or recombinant tvb polypeptide having a molecular weight of about 42 kd including a signal sequence, e.g, in the range of 39 kd to 49 kd. In other embodiments, the peptide core of a mature tvb protein preferably has a molecular weight of about 39 kD. It will be understood that certain post-translational modifications, e.g., glycosylation and the like, can increase the apparent molecular weight of the tvb protein relative to the unmodified polypeptide chain.

The subject proteins can also be provided as chimeric molecules, such as in the form of fusion proteins. For instance, the tvb protein can be provided as a recombinant fusion protein which includes a second polypeptide portion, e.g., a second polypeptide having an amino acid sequence unrelated (heterologous) to the tvb polypeptide, e.g. the second polypeptide portion is glutathione-S-transferase, e.g. the second polypeptide portion is an enzymatic activity such as alkaline phosphatase, e.g. the second polypeptide portion is an epitope tag.

In yet another embodiment, the invention features a nucleic acid encoding a tvb polypeptide, which has the ability to modulate, e.g., either mimic or antagonize, at least a portion of the activity of a wild-type tvb polypeptide. An exemplary tvb-encoding nucleic acid sequence is represented by SEQ ID No: 1.

In another embodiment, the nucleic acid of the present invention includes a coding sequence which hybridizes under stringent conditions with the coding sequence designated in SEQ ID No: 1. The coding sequence of the nucleic acid can comprise a sequence which is identical to a coding sequence represented in of SEQ ID No: 1, or it can merely be homologous to that sequences. In preferred embodiments, the nucleic acid encodes a polypeptide which specifically modulates, by acting as either an agonist or antagonist, one or more of the bioactivities of a wild-type tvb polypeptides.

Furthermore, in certain preferred embodiments, the subject tvb nucleic acid will include a transcriptional regulatory sequence, e.g. at least one of a transcriptional promoter or transcriptional enhancer sequence, which regulatory sequence is operably linked to the tvb gene sequence. Such regulatory sequences can be used in to render the tvb gene sequence suitable for use as an expression vector. This invention also contemplates the cells transfected with said expression vector whether prokaryotic or eukaryotic and a method for producing tvb proteins by employing said expression vectors.

In yet another embodiment, the nucleic acid hybridizes under stringent conditions to a nucleic acid probe corresponding to at least 12 consecutive nucleotides of either sense or antisense sequence of SEQ ID No: 1; though preferably to at least 25 consecutive nucleotides; and more preferably to at least 40, 50 or 75 consecutive nucleotides of either sense or antisense sequence of SEQ ID No: 1.

Yet another aspect of the present invention concerns an immunogen comprising a tvb polypeptide in an immunogenic preparation, the immunogen being capable of eliciting an immune response specific for a tvb polypeptide; e.g. a humoral response, e.g. an antibody response; e.g. a cellular response. In preferred embodiments, the immunogen comprising an antigenic determinant, e.g. a unique determinant, from the protein represented by SEQ ID No. 2.

A still further aspect of the present invention features antibodies and antibody preparations specifically reactive with an epitope of the tvb immunogen.

The invention also features transgenic non-human animals, e.g. mice, rats, rabbits, chickens, frogs or pigs, having a transgene, e.g., animals which include (and preferably express) a heterologous form of a tvb gene described herein, or which misexpress an endogenous tvb gene, e.g., an animal in which expression of one or more of the subject tvb proteins is disrupted. Such a transgenic animal can serve as an animal model for studying cellular and tissue disorders comprising mutated or mis-expressed tvb alleles or for use in drug screening. Moreover, as described herein, such transgenic animals can be used to direct delivery of second recombinant gene construct which is delivered by infection with a recombinant ALSV which includes a second gene of interest, e.g., the expression of the tvb transgene determining the tissue infection spectrum of the recombinant ALSV.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequence of SEQ ID No: 1, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a tvb protein, such as for detecting in a sample of cells isolated from a patient, a level of a nucleic acid encoding a tvb protein; e.g. measuring a tvb MRNA level in a cell, or determining whether a genomic tvb gene has been mutated or deleted. These so-called “probes/primers” of the invention can also be used as a part of “antisense” therapy which refers to administration or in situ generation of oligonucleotide probes or their derivatives which specifically hybridize (e.g. bind) under cellular conditions, with the cellular mRNA and/or genomic DNA encoding one or more of the subject tvb proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between a tvb protein and, for example, a virus, an extracellular ligand of the tvb protein, or an intracellular protein which binds to the tvb protein, eg., a TRAF protein. An exemplary method includes the steps of (i) combining a tvb polypeptide or bioactive fragments thereof, a tvb target polypeptide (such as an ALSV viral protein), and a test compound, e.g., under conditions wherein, but for the test compound, the tvb protein and target polypeptide are able to interact; and (ii) detecting the formation of a complex which includes the tvb protein and the target polypeptide either by directly quantitating the complex, or by measuring inductive effects of the tvb protein. A statistically significant change, such as a decrease, in the formation of the complex in the presence of a test compound (relative to what is detected in the absence of the test compound) is indicative of a modulation, e.g., inhibition or potentiation, of the interaction between the tvb protein and its target polypeptide.

Yet another aspect of the present invention concerns a method for modulating one or more of growth, differentiation, or survival of a cell by modulating tvb bioactivity, e.g., by potentiating or disrupting certain protein-protein interactions. In general, whether carried out in vivo, in vitro, or in situ, the method comprises treating the cell with an effective amount of a tvb therapeutic so as to alter, relative to the cell in the absence of treatment, at least one of (i) rate of growth, (ii) differentiation, or (iii) survival of the cell. Accordingly, the method can be carried out with tvb therapeutics such as peptide and peptidomimetics or other molecules identified in the above-referenced drug screens which agonize or antagonize the effects of signaling from a tvb protein or viral binding of a tvb protein. Other tvb therapeutics include antisense constructs for inhibiting expression of tvb proteins, and dominant negative mutants of tvb proteins which competitively inhibit ligand interactions upstream and signal transduction downstream of the wild-type tvb protein.

Illustrative embodiments utilize an apoptosis regulating composition in the treatment of, for example, retrovirus-related disease including AIDS, ARC (AIDS related complex), ATL (adult T cell leukemia), hairy cell leukemia, myelopathy (HAM/TSP), respiratory disorder (HAB/HABA), arthropathy (HAAP), HIV- or HTLV-I (human T cell leukemia virus type I)-related diseases such as uveitis (HAU), and C-type hepatitis; autoimmune diseases including collagen diseases such as SLE (systemic lupus erythematosus) and rheumatoid arthritis (RA), ulcerative colitis, Sjogren’s syndrome, primary biliary hepatic cirrhosis, idiopathic thrombocytopenic purpura (ITP), autoimmune hemolytic anemia, myasthenia gravis, Hashimoto’s disease and insulin dependent (type I) diabetes mellitus; diseases accompanied by thrombocytopenia, for example, myelodysplastic syndrome (MDS), periodic thrombocytopenia, aplastic anemia, idiopathic thrombocytopenia and disseminated intravascular coagulation; liver diseases such as viral or drug-induced hepatitis (such as types C, A, B, and F) and hepatic cirrhosis; neurodegenerative disorders, such as Alzheimer’s disease (AD), Huntington’s disease (HD) and Parkinson’s disease; myocarditis; ARDS (adult respiratory distress syndrome); infectious diseases; prostatic hypertrophy; uterine myoma; bronchial asthma; arteriosclerosis; congenital malformations; nephritis; senile cataract; chronic fatigue syndrome (CFS); and myotonic dystrophy.

The present method is applicable, for example, to cell culture technique, such as in the culturing of hematopoietic cells and other cells whose survival or differentiative state is dependent on tvb function. Moreover, tvb agonists and antagonists can be used for therapeutic intervention, such as to enhance survival and maintenance of cells, as well as to influence organogenic pathways, such as tissue patterning and other differentiation processes. In an exemplary embodiment, the method is practiced for modulating, in an animal, cell growth, cell differentiation or cell survival, and comprises administering a therapeutically effective amount of a tvb therapeutic to alter, relative the absence of tvb treatment, at least one of (i) rate of growth, (ii) differentiation, or (iii) survival of one or more cell-types in the animal.

Another aspect of the present invention provides a method of determining if a subject, e.g. an animal patient, is at risk for a disorder characterized by unwanted cell proliferation or aberrant control of differentiation or apoptosis. The method includes detecting, in a tissue of the subject, the presence or absence of a genetic lesion characterized by at least one of (i) a mutation of a gene encoding a tvb protein, e.g. represented in SEQ ID No: 1 or a homolog thereof; or (ii) the mis-expression of a tvb gene. In preferred embodiments, detecting the genetic lesion includes ascertaining the existence of at least one of: a deletion of one or more nucleotides from a tvb gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble tvb protein.

For example, detecting the genetic lesion can include (i) providing a probe/primer including an oligonucleotide containing a region of nucleotide sequence which hybridizes to a sense or antisense sequence of a tvb gene or naturally occurring mutants thereof, or 5' or 3' flanking sequences naturally associated with the tvb gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the tvb gene and, optionally, of the flanking nucleic acid sequences. For instance, the probe/primer can be employed in a polymerase chain reaction (PCR) or in a ligation chain reaction (LCR). In alternate embodiments, the level of a tvb protein is detected in an immunoassay using an antibody which is specifically immunoreactive with the tvb protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Transcription And Translation (B. D. Hames & S. J. Higgins eds. 1984 IRL Press, Washington, D.C.); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 3 is a sequence alignment of the death domains of tvb, TNF-RI and Fas.

FIG. 5 demonstrates that the putative tvb protein confers susceptibility to ALV-B infection and increases susceptibility to infection by mammal-tropic ALV-D.

DETAILED DESCRIPTION OF THE INVENTION

Figure 1:
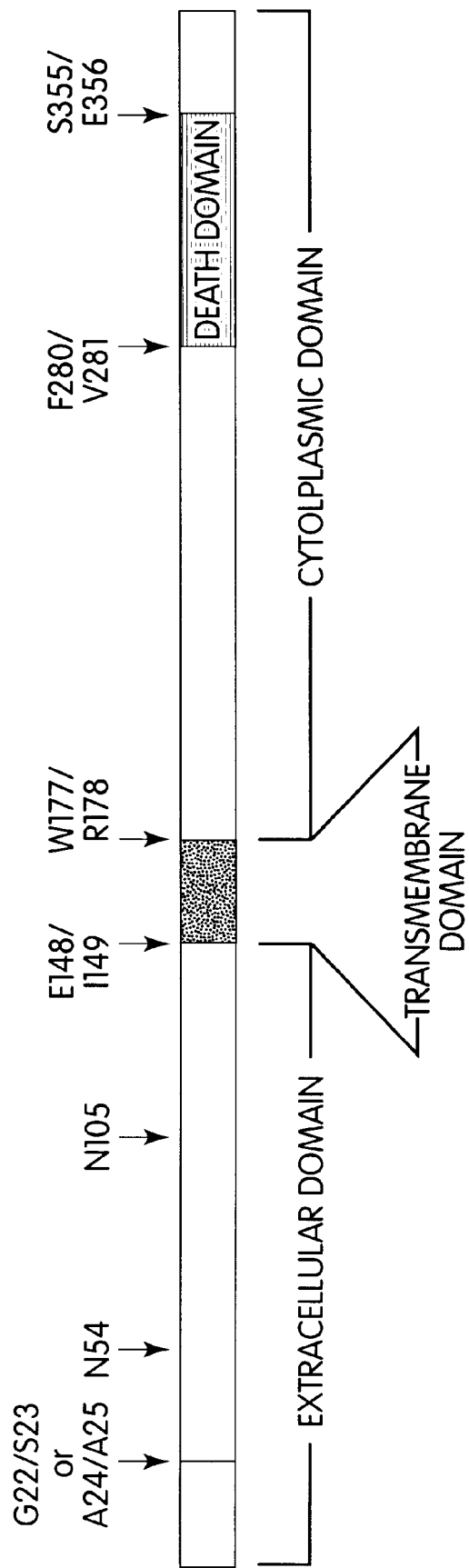
FIG. 1 is a schematic representation of the domain/motif structure of the tvb receptor protein.

Members of the TNF superfamily are known to be among the most pleiotropic cytokines, signaling a large number of cellular responses, including cytotoxicity, anti-viral activity, immunoregulatory activities, and the transcriptional activation of many genes. The first step in the induction of the various cellular responses mediated by these cytokines is their binding to specific cell surface receptors. The binding to these receptors of their respective ligands induces receptor oligomerization and activation of signal transduction pathways.

The present invention concerns the discovery of a new member of the TNF receptor superfamily, referred to herein as the candidate "tvb receptor". Experimental evidence suggests that the instant gene corresponds to the gene of the $tvb^{s3}$ locus responsible for mediating certain viral infection, and demonstrates a functional role for the tvb gene product as the receptor for certain of the avian leukosis/sarcoma viruses (ALSV) in avians. Moreover, inspection of the tvb sequence, particularly in comparison with other TNF receptors, reveals the presence of a "death domain" in the cytoplasmic tail of the tvb receptor, suggesting a role for the tvb receptor in determining tissue fate and maintenance. For instance, the proteins encoded by the tvb genes may participate, under various circumstances, in the control of proliferation, differentiation and/or cell death.

As described in further detail in the appended examples, in order to study the mechanism of entry used by cytopathic subgroups of ALSV, we attempted to isolate the gene(s) of the chicken $tvb^{s3}$ locus predicted to encode receptors for ALSV-B and ALSV-D subtypes. Genomic DNA from C/E chicken cells that are homozygous for $tvb^{s3s3}$ was transfected into mammalian cells, and transfectants that became susceptible to ALSV-B were identified by infection with subgroup B RCAS viral vectors containing selectable marker genes. Southern blot analysis of multiple independent secondary transfectants revealed the presence of a shared 7.5 kb chicken DNA locus, presumably $tvb^{s3s3}$. Indeed, a 9 kb genomic DNA fragment derived from the shared locus was isolated and shown to confer susceptibility to ALSV-B infection after transfection into human cells. Northern blot analysis of polyadenylated RNA from C/E chicken embryo fibroblasts using radioactively labeled probes from the cloned gene revealed a single mRNA species of 2.3 kb. In addition, a similarly sized mRNA transcript was detected in turkey and quail fibroblasts which are infectable by ALSV-E, but not ALSV-B or ALSV-D.

A 2.3 kb cDNA clone was isolated from a C/E chicken cell cDNA library by screening with probes from the genomic DNA clone. The sequence of the chicken tvb cDNA clone is provided in SEQ ID No. 1. The cDNA clone, when expressed in transfected COS cells, conferred susceptibility of these cells to ALSV-B infection, increased susceptibility to ALSV-D infection, but did not allow infection of subgroup A or C viruses. These results indicate that the cloned gene is $tvb^{s3}$.

Figure 2:
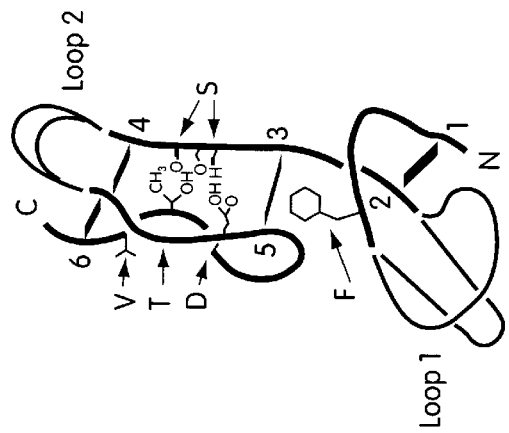
FIG. 2 is a sequence alignment of the CRDs of tvb, TNF-RI and Fas.

The functional cDNA cloned encodes a 368 amino acid type I membrane protein (see SEQ ID No. 2). Analysis of the cloned tvb sequence revealed certain similarities to known domains or motifs of previously identified proteins from the TNF receptor superfamily, and was significantly similar to the TNF-RI and Fas receptor types. As illustrated in FIG. 1, the overall structure of the tvb protein is predicted to have an extracellular domain spanning from Met1 to Glu148, a transmembrane domain including amino acid residues Ile149 to Trp177, and a cytoplasmic domain including Arg178 to Ser368. The protein sequence is predicted to include a secretion signal sequence including Met1 to one or either Gly22 or Ala24. Thus, the mature protein begins at either Ser23 or Ala25 to yield a 344–346 amino acid protein. The extracellular architecture of the tvb protein is characteristic of the larger TNFR superfarnily, containing two of the extracellular CRD's (Cys59-Cys101 and Cys103-Cys143), as compared to four CRD's in each of TNF-RI and Fas (See FIG. 2). The mature protein is also expected to include N-linked glycosylated residues at Asn54 and Asn105.

Moreover, the cytoplasmic domain of the tvb receptor contains a region of significant similarity to the "death domain" regions of Fas and TNIR-I. See FIG. 3. The presence of this domain, spanning Val281-Ser355, suggest that the tvb protein might participate in cell killing events associated with subgroup B and D viral infections or other ligand engagement events. As described in the example below, in order to test this idea we constructed a soluble immunoadhesion molecule comprising the subgroup B RAV-2 SU envelope protein fused to the constant regions of an immunoglobulin. Binding of the viral protein to the tvb protein results in cross-linking of the receptor, and in similar fashion to ligand-induced cross-linking of Fas and TNF-RI, the immunoadhesion resulted in apoptosis of an avian cells expressing the tvb protein; in cells which express a tvb allele which doesn't allow ALSV entry, apoptosis was not observed, indicating that tvb cross-linking is required for the apoptotic signal. By analogy to TNF-RI and Fas, the death domain of tvb is believed to function as an adaptor to couple the tvb receptor to other signaling molecules.

The fact that the tvb protein can: (i) engage intracellular signal proteins involved in cell killing, e.g., presumably members of the TNFR-asociated factors (TRAF) superfamily, (ii) the infectivity of certain mammalian cells by ALSV-D (Johnson et al. (1994) Cancer Det Preven 18:9–30), and (iii) certain similarities in pathogenesis of mammalian cell infections, e.g., with feline leukemia viruses, suggests that the tvb gene and gene products are conserved amongst other animals, including mammals.

Accordingly, certain aspects of the present invention relate to nucleic acids encoding tvb proteins, the tvb proteins themselves (including various fragments), antibodies immunoreactive with tvb proteins, and preparations of such compositions. Moreover, the present invention provides diagnostic and therapeutic assays and reagents for detecting and treating disorders involving, for example, aberrant expression (or loss thereof) of tvb homologs.

In addition, drug discovery assays are provided for identifying agents which can modulate the biological function of tvb proteins, such as by altering the binding of tvb molecules to other cellular or viral proteins. Such agents can be useful therapeutically to alter the growth and/or differentiation of a cell, or viral infectivity of the cell. Other aspects of the invention are described below or will be apparent to those skilled in the art in light of the present disclosure.

The interaction of tvb proteins with TRAFs or other signal transduction proteins represents yet another therapeutic target. Accordingly, drug discovery assays are provided for identifying agents which can modulate the interaction of TRAF polypeptides and the like with tvb polypeptides. For instance, such assays can be derived to detect the ability of a test agent to alter protein-protein contacts. Agents which modulate these interactions can be useful therapeutically to alter the growth, survival and/or differentiation of cells.

For convenience, certain terms employed in the specification, examples, and appended claims are collected here.

The term "cysteine rich domain" or "CRD" refers to motifs present in the extracellular domain of the tvb receptor and presumably important in ligand binding and conserved in other members of the TNFR superfamily. See FIG. 2. Each of the CRDs are characterized by the presence of approximately 6 cysteine residues that are interspersed within a stretch of 40 amino acids.

As used herein, the term "death domain" refers to a motif of amino acid sequences present in cytoplasmic domain of such TNFR family members as TNF-RI, Fas and the instant tvb receptor, which motif is required for induction of apoptosis under certain circumstances of receptor engagement. The death domain of tvb corresponds to Val281-Ser355 of SEQ ID No. 2. See FIG. 3.

The term "TNFR-associated factor superfamily" or "TRAF proteins", refers to intracellular proteins which interact with TNFR proteins such as TNF-RI, Fas and/or tvb by virtue of the death domains of those receptors. The TRAF superfamily, according to the present application, includes such as the TRADDs, RIPs, FADDs, TRAF1, TRAF2 and the like, e.g., which bind to the death domain of a TNFR-related protein and thereby inhibit or induce an intracellular signal.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding of a tvb polypeptide, including both exon and (optionally) intron sequences. A "recombinant gene" refers to nucleic acid encoding a tvb polypeptide and comprising tvb-encoding exon sequences, though it may optionally include intron sequences which are derived from, for example, a chromosomal tvb gene or from an unrelated chromosomal gene. Exemplary recombinant genes encoding the subject tvb polypeptide are represented in the appended Sequence Listing. The term "intron" refers to a DNA sequence present in a given tvb gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a tvb polypeptide or, where anti-sense expression occurs from the transferred gene, the expression of a naturally-occurring form of the tvb protein is disrupted.

As used herein, the term "specifically hybridizes" refers to the ability of a nucleic acid probe/primer of the invention to hybridize to at least 15 consecutive nucleotides of a tvb gene, such as a tvb sequence designated in SEQ ID No: 1, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a tvb protein, as defined herein. In preferred embodiments, the oligonucleotide probe specifically detects only a tvb gene, e.g., it does not substantially hybridize to transcripts for other TNF receptor homologs, such as TNFR1, fas or CD40.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant tvb gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of tvb genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neuronal or hematopoietic origin. The term also covers so-called "leaky" promoters, which regulate expression of a selected DNA primarily in one tissue, but can cause at least low level expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by rnicroinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In an exemplary transgenic animal, the transgene causes cells to express a recombinant form of a tvb protein, e.g. either agonistic or antagonistic forms. However, transgenic animals in which the recombinant tvb gene is silent are also contemplated, as for example, the FLP or CRE recombinase dependent constructs described below. Moreover, "transgenic animal" also includes those recombinant animals in which gene disruption of one or more tvb genes is caused by human intervention, including both recombination and antisense techniques.

The "non-human animals" of the invention include vertebrates such as rodents, non-human primates, livestock, avian species, amphibians, reptiles, etc. The term "chimeric animal" is used herein to refer to animals in which the recombinant gene is found, or in which the recombinant is expressed in some but not all cells of the animal. The term "tissue-specific chimeric animal" indicates that a recombinant tvb genes is present and/or expressed or disrupted in some tissues but not others.

The term "avian species" includes chicken, quail, turkey, duck and other fowl.

The term "transgenic chicken" refers to a chicken that contains a transferred nucleic acid sequence, including a transferred protein-encoding and/or regulatory sequence, such that the transferred sequence is integrated into a host chromosome. As a result of such transfer and integration, the transferred sequence may be transmitted through germ cells to the offspring of a transgenic chicken. Thus, transgenic chickens are created by introducing by a method of transfer, new nucleic acid sequences into germ cells.

As used herein, the term "transgene" means a nucleic acid sequence (encoding, e.g., a tvb polypeptide, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a tvb polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with a tvb sequence of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding a tvb polypeptide with a second amino acid sequence defining a domain (e.g. polypeptide portion) foreign to and not substantially homologous with any domain of a tvb protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-tvb-Y, wherein tvb represents a portion of the fusion protein which is derived from a tvb protein, and X and Y are, independently, absent or represent amino acid sequences which are not related to a tvb sequences in an organism.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding a tvb polypeptide preferably includes no more than 10 kilobases (kb) of nucleic acid sequence which naturally immediately flanks the tvb gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding tvb polypeptides, and/or equivalents of such nucleic acids. The term nucleic acid as used herein is intended to include fragments as equivalents. The term equivalent is understood to include nucleotide sequences encoding functionally equivalent tvb polypeptides or functionally equivalent peptides having an activity of a tvb protein such as described herein. Equivalent nucleotide sequences will include sequences that differ by one or more nucleotide substitutions, additions or deletions, such as allelic variants; and will, therefore, include sequences that differ from the nucleotide sequence of the tvb cDNA sequence shown in SEQ ID No: 1 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequences represented in SEQ ID No: 1. In one embodiment, equivalents will further include nucleic acid sequences derived from and evolutionarily related to, a nucleotide sequences shown in SEQ ID No: 1.

Moreover, it will be generally appreciated that, under certain circumstances, it may be advantageous to provide homologs of a tvb polypeptide which function in a limited capacity as one of either a tvb agonist (mimetic) or a tvb antagonist, in order to promote or inhibit only a subset of the biological activities of the naturally-occurring form of the protein. Thus, specific biological effects can be elicited by treatment with a homolog of limited function. For example, as described below, transgenic avian species can be generated to express a mutant tvb protein which performs substantially all other functions of the naturally occurring protein with the exception that it will not bind ALSV.

Homologs of the subject tvb protein can be generated by mutagenesis, such as by discrete point mutation(s), or by truncation. For instance, mutation can give rise to homologs which retain substantially the same, or merely a subset, of the biological activity of the tvb polypeptide from which it was derived. Alternatively, antagonistic forms of the protein can be generated which are able to inhibit the function of the naturally occurring form of the protein, such as by competitively binding to a tvb substrate or tvb associated protein, as for example competing with wild-type tvb in the binding of a viral protein, a cellular protein such as a TRAF. Thus, the tvb protein and homologs thereof provided by the subject invention may be either positive or negative regulators of viral infection, cell growth, death and/or differentiation.

In general, polypeptides referred to herein as having an activity of a tvb protein (e.g., are "bioactive") are defined as polypeptides which include an amino acid sequence corresponding (e.g., identical or homologous) to all or a portion of the amino acid sequences of the tvb protein shown in SEQ ID No: 2, and which mimic or antagonize all or a portion of the biological/biochemical activities of a naturally occurring tvb protein. Examples of such biological activity include: the ability to bind to a viral coat protein, e.g., an env protein of an ALSV, e.g., of ALSV-B or ALSV-D; the ability to confer viral infectivity on a cell, e.g., susceptibility to infection by an ALSV; the ability to bind to intracellular proteins which interact with the death domain of the tvb protein, e.g., proteins involved in signaling apoptosis, e.g., TNFR-associated factors and the like; and/or the ability to induce apoptosis upon receptor cross-linking. For example, inhibiting interaction of a tvb receptor with a TRAF protein can be used to rescue a cell from apoptosis or other fate mediated by signal transduction through the TRAF. The bioactivity of certain embodiments of the tvb protein can be characterized in terms of an ability to bind to a virus, such as an ALSV.

Other biological activities of the subject tvb proteins are described herein or will be reasonably apparent to those skilled in the art. According to the present invention, a polypeptide has biological activity if it is a specific agonist or antagonist of a naturally-occurring form of a tvb protein.

Preferred nucleic acids encode a tvb polypeptide comprising an amino acid sequence at least 70% homologous, more preferably at least 80% homologous and most preferably at least 85% homologous with an amino acid sequence of a naturally occurring tvb protein, e.g., such as represented in SEQ ID No: 2. Nucleic acids which encode polypeptides at least about 90%, more preferably at least about 95%, and most preferably at least about 98–99% homology with an amino acid sequence represented in SEQ ID No: 2 are of course also within the scope of the invention, as are nucleic acids identical in sequence with the enumerated tvb sequence of the sequence listing. In one embodiment, the nucleic acid is a cDNA encoding a polypeptide having at least one activity of the subject tvb polypeptide.

In certain preferred embodiments, the invention features a purified or recombinant tvb polypeptide having peptide chain with a molecular weight in the range of 39 kd to 49 kd, even more preferably in the range of 39–43 kd. It will be understood that certain post-translational modifications, e.g., glycosylation, phosphorylation and the like, can increase the apparent molecular weight of the tvb protein relative to the unmodified polypeptide chain, and cleavage of certain sequences, such as pro-sequences, can likewise decrease the apparent molecular weight. In a preferred embodiments, the nucleic acid encodes a tvb polypeptide which includes two cysteine motifs, and preferably possesses a death domain.

Another aspect of the invention provides a nucleic acid which hybridizes under high or low stringency conditions to the nucleic acid represented by SEQ ID No: 1. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C.

Nucleic acids having a sequence that differs from the nucleotide sequences shown in SEQ ID No: 1 due to degeneracy in the genetic code are also within the scope of the invention. Such nucleic acids encode functionally equivalent peptides (i.e., a peptide having a biological activity of a tvb polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a tvb polypeptide. However, it is expected that DNA sequence polymorphisms that do lead to changes in the amino acid sequences of the subject tvb polypeptides will exist among, for example, humans. One skilled in the art will appreciate that these variations in one or more nucleotides (up to about 3–5% of the nucleotides) of the nucleic acids encoding polypeptides having an activity of a tvb polypeptide may exist among individuals of a given species due to natural allelic variation.

As used herein, a tvb gene fragment refers to a nucleic acid having fewer nucleotides than the nucleotide sequence encoding the entire mature form of a tvb protein yet which (preferably) encodes a polypeptide which retains some biological activity of the fall length protein. Fragment sizes contemplated by the present invention include, for example, 5, 10, 25, 50, 75, 100, or 200 amino acids in length. In a preferred embodiment of truncated receptors, the polypeptide will include all or a sufficient portion of the extracellular domain to bind to a tvb ligand or viral protein (such as ALSV-B or ALSV-D), e.g., the cysteine rich motifs. In another preferred embodiment, the truncated tvb protein will include all or at least the death domain of the cytosolic portion of the protein. In either embodiment, the tvb polypeptide can also include the transmembrane domain, particularly where membrane localized (instead of soluble) fragments of the tvb protein are desired.

As indicated by the examples set out below, tvb protein-encoding nucleic acids can be obtained from mRNA present in cells of metazoan organisms. It should also be possible to obtain nucleic acids encoding tvb polypeptides of the present invention from genomic DNA from both adults and embryos. For example, a gene encoding a tvb protein can be cloned from either a cDNA or a genomic library in accordance with protocols described herein, as well as those generally known to persons skilled in the art. A cDNA encoding a tvb protein can be obtained by isolating total mRNA from a cell, such as a mammalian cell, e.g. a human cell, as desired. Double stranded cDNAs can be prepared from the total mRNA, and subsequently inserted into a suitable plasmid or bacteriophage vector using any one of a number of known techniques. The gene encoding a tvb protein can also be cloned using established polymerase chain reaction techniques in accordance with the nucleotide sequence information provided by the invention. The nucleic acid of the invention can be DNA or RNA. A preferred nucleic acid is a cDNA including a nucleotide sequence represented by one of SEQ ID No: 1.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding a subject tvb protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a tvb protein. Alternatively, the antisense construct is an oligonucleotide probe which is generated ex vivo and which, when introduced into the cell causes inhibition of expression by hybridizing with the mRNA and/or genomic sequences of a tvb gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775), or peptide nucleic acids (PNAs). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of a tvb protein, can be used in the manipulation of tissue, e.g. tissue maintenance, differentiation or growth, both in vivo and ex vivo.

Furthermore, the anti-sense techniques (e.g. microinjection of antisense molecules, or transfection with plasmids whose transcripts are anti-sense with regard to a tvb mRNA or gene sequence) can be used to investigate the role of tvb in developmental events, as well as the normal cellular function of tvb in adult tissue. Such techniques can be utilized in cell culture, but can also be used in the creation of transgenic animals (described infra).

This invention also provides expression vectors containing a nucleic acid encoding a tvb polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject tvb proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding tvb polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage $\lambda$, the control regions for fd coat protein, the promoter for 3-phosphoglycerate kinase or other glycolytic enzymes, the promoters of acid phosphatase, e.g., Pho5, the promoters of the yeast $\alpha$-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a polypeptide having an agonistic activity of a subject tvb polypeptide, or alternatively, encoding a polypeptide which is an antagonistic form of the tvb protein, such as a soluble truncated form of the extracellular domain, or a truncated form of the intracellular domain. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids, e.g., encoding either an agonistic or antagonistic form of a subject tvb proteins or an antisense molecule described above. Thus, another aspect of the invention features expression vectors for in vivo or in vitro transfection and expression of a tvb polypeptide or antisense molecule in particular cell types so as to reconstitute the function of, or alternatively, abrogate all or a portion of the biological function of tvb-induced transcription in a tissue in which the naturally-occurring form of the protein is misexpressed (or has been disrupted); or to deliver a form of the protein which alters maintenance or differentiation of tissue, or which inhibits neoplastic or hyperplastic proliferation.

Expression constructs of the subject tvb polypeptides, as well as antisense constructs, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of tvb expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA encoding the particular tvb polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retrovirus vectors, adenovirus vectors and adenoassociated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to viral transfer methods, such as those illustrated above, non-viral methods can also be employed to cause expression of a subject tvb polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject tvb polypeptide gene by the targeted cell. Exemplary gene delivery systems of this type include liposomal derived systems, poly-lysine conjugates, and artificial viral envelopes.

In clinical settings, the gene delivery systems for the therapeutic tvb gene can be introduced into a patient-animal by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91:3054–3057). A tvb gene can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the tvb proteins. Recombinant polypeptides preferred by the present invention, in addition to native tvb proteins, are at least 70% homologous, more preferably at least 80% homologous and most preferably at least 85% homologous with an amino acid sequence represented by SEQ ID No: 2. Polypeptides which possess an activity of a tvb protein (i.e. either agonistic or antagonistic), and which are at least 90%, more preferably at least 95%, and most preferably at least about 98–99% homologous with SEQ ID No: 2 are also within the scope of the invention. Such polypeptides, as described above, include various truncated forms of the protein.

The term "recombinant tvb protein" refers to a polypeptide which is produced by recombinant DNA techniques, wherein generally, DNA encoding a tvb polypeptide is inserted into a suitable expression vector which is in turn used to transform a host cell to produce the heterologous protein. Moreover, the phrase "derived from", with respect to a recombinant tvb gene, is meant to include within the meaning of "recombinant protein" those proteins having an amino acid sequence of a native tvb protein, or an amino acid sequence similar thereto which is generated by mutations including substitutions and deletions (including truncation) of a naturally occurring form of the protein.

The present invention further pertains to recombinant forms of the subject tvb polypeptides which are encoded by genes derived from a manmal (e.g. a human), reptile or amphibian and which have amino acid sequences evolutionarily related to the tvb protein represented in SEQ ID No: 2. Such recombinant tvb polypeptides preferably are capable of functioning in one of either role of an agonist or antagonist of at least one biological activity of a wild-type ("authentic") tvb protein of the appended sequence listing. The term "evolutionarily related to", with respect to amino acid sequences of tvb proteins, refers to both polypeptides having amino acid sequences which have arisen naturally, and also to mutational variants of tvb polypeptides which are derived, for example, by combinatorial mutagenesis.

The present invention also provides methods of producing the subject tvb polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant tvb polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant tvb polypeptide is a fusion protein containing a domain which facilitates its purification, such as GST fusion protein or poly(His) fusion protein.

This invention also pertains to a host cell transfected to express recombinant forms of the subject tvb polypeptides. The host cell may be any eukaryotic or prokaryotic cell. Thus, a nucleotide sequence derived from the cloning of tvb proteins, encoding all or a selected portion of a full-length protein, can be used to produce a recombinant form of a tvb polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinases, p53, WT1, PTP phosphatases, SRC, and the like. Similar procedures, or modifications thereof, can be employed to prepare recombinant tvb polypeptides by microbial means or tissue-culture technology in accord with the subject invention.

The recombinant tvb genes can be produced by ligating nucleic acid encoding an tvb protein, or a portion thereof, into a vector suitable for expression in either prokaryotic cells, eukaryotic cells, or both. Expression vectors for production of recombinant forms of the subject tvb polypeptides include plasmids and other vectors. For instance, suitable vectors for the expression of a tvb polypeptide include plasmids of the types: pBR322-derived plasmids, pEMBL-derived plasmids, pEX-derived plasmids, pBTac-derived plasmids and pUC-derived plasmids for expression in prokaryotic cells, such as *Escherichia coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *Saccharomyces cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a tvb polypeptide is produced recombinantly utilizing an expression vector generated by sub-cloning the coding sequence of a tvb gene represented in SEQ ID No: 1.

The preferred manmmalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant tvb polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a tvb protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *Salmonella typhimurium* and its in vitro activity has been demonstrated on recombinant proteins (Miller et al. (1987) PNAS 84:2718–1722). Therefore, removal of an N-terminal methionine, if desired, can be achieved either in vivo by expressing tvb-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a tvb protein. For example, the VP6 capsid protein of rotavirus can be used as an immunologic carrier protein for portions of the tvb polypeptide, either in the monomeric form or in the form of a viral particle. The nucleic acid sequences corresponding to the portion of a subject tvb protein to which antibodies are to be raised can be incorporated into a fusion gene construct which includes coding sequences for a late vaccinia virus structural protein to produce a set of recombinant viruses expressing fusion proteins comprising tvb epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a tvb protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a tvb polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of tvb proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the tvb polypeptides of the present invention, particularly truncated forms of the tvb protein. For example, tvb polypeptides can be generated as glutathione-S-transferase (GST-fusion) proteins. Such GST-fusion proteins can enable easy purification of the tvb polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termin, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The tvb polypeptides may also be chemically modified to create tvb derivatives by forming covalent or aggregate conjugates with other chemical moieties, such as glycosyl groups, lipids, phosphate, acetyl groups and the like. Covalent derivatives of tvb proteins can be prepared by linking the chemical moieties to fluctional groups on amino acid sidechains of the protein or at the N-terminus or at the C-terminus of the polypeptide.

The present invention also makes available isolated tvb polypeptides which are isolated from, or otherwise substantially free of other cellular proteins, especially other signal transduction factors membrane-localized proteins which may normally be associated with the tvb polypeptide. The term "substantially free of other cellular proteins" (also referred to herein as "contaminating proteins") or "substantially pure or purified preparations" are defined as encompassing preparations of tvb polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified tvb preparations will lack any contaminating proteins from the same animal from that tvb is normally produced, as can be accomplished by recombinant expression of, for example, an avian tvb protein in a mammalian cell.

As described above for recombinant polypeptides, isolated tvb polypeptides can include all or a portion of an amino acid sequences corresponding to a tvb polypeptide represented in SEQ ID No: 2 or homologous sequences thereto.

Isolated peptidyl portions of tvb proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a tvb polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") tvb protein.

The recombinant tvb polypeptides of the present invention also include homologs of the authentic tvb proteins, such as versions of those protein which are resistant to proteolytic cleavage, as for example, due to mutations which alter ubiquitination or other enzymatic targeting associated with the protein.

Modification of the structure of the subject tvb polypeptides can be for such purposes as enhancing therapeutic or prophylactic efficacy, stability (e.g., ex vivo shelf life and resistance to proteolytic degradation in vivo), or post-translational modifications (e.g., to alter glycosylation or phosphorylation patterns of protein). Such modified peptides, when designed to retain at least one activity of the naturally-occurring form of the protein, or to produce specific antagonists thereof, are considered functional equivalents of the tvb polypeptides (though they may be agonistic or antagonistic of the bioactivities of the authentic protein). Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containg= cysteine and methionine. (see, for example, Biochemistry, 2nd ed., Ed. by L. Stryer, W H Freeman and Co.: 1981). Whether a change in the amino acid sequence of a peptide results in a functional tvb homolog (e.g. functional in the sense that the resulting polypeptide mimics or antagonizes the authentic form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject tvb proteins as well as truncation mutants, and is especially usefuil for identifying potential variant sequences (e.g. homologs) that are functional in modulating signal transduction and/or viral infectivity. The purpose of screening such combinatorial libraries is to generate, for example, novel tvb homologs which can act as either agonists or antagonist, or alternatively, possess novel activities all together. To illustrate, tvb homologs can be engineered by the present method to provide selective, constitutive activation of apoptotic activity, or alternatively, to be dominant negative inhibitors of tvb-dependent apoptosis.

Likewise, tvb homologs can be generated by the present combinatorial approach to selectively inhibit (antagonize) the wild-type receptor. For instance, mutagenesis can provide tvb homologs which are able to bind extracellular ligands and/or regulatory proteins yet been unable to bind to virus which otherwise bind the authentic form of the receptor, e.g. reduced binding to ALSV-B and/or ALSV-D. In yet other embodiments, a dominant negative mutant of a tvb protein is mutated at one or more residues to prevent binding to TRAFs or other proteins containing death domains.

In one aspect of this method, the amino acid sequences for a population of tvb homologs or other related proteins are aligned, preferably to promote the highest homology possible. Such a population of variants can include, for example, tvb homologs from one or more species. Amino acids which appear at each position of the aligned sequences are selected to create a degenerate set of combinatorial sequences. In a preferred embodiment, the variegated library of tvb variants is generated by combinatorial mutagenesis at the nucleic acid level, and is encoded by a variegated gene library. For instance, a mixture of synthetic oligonucleotides can be enzymatically ligated into gene sequences such that the degenerate set of potential tvb sequences are expressible as individual polypeptides, or alternatively, as a set of larger fusion proteins (e.g. for phage display) containing the set of tvb sequences therein.

There are many ways by which such libraries of potential tvb homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential tvb sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87:6378–6382; as well as U.S. Pat. Nos. 5,223,409, 5,198,346, and 5,096,815).

Likewise, a library of coding sequence fragments can be provided for a tvb clone in order to generate a variegated population of tvb fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a tvb coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of tvb homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an exemplary embodiment, a library of variants derived from a truncated extracellular domain which are mutated, e.g., by alanine scanning mutagenesis, is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd., and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

For example, the recombinant phage antibody system (RPAS, Pharmacia Catalog number 27-9400-01) can be easily modified for use in expressing and screening tvb combinatorial libraries by panning on glutathione immobilized ALSV coat protein/GST fusion proteins to enrich, in the flow through, for tvb homologs with reduced ability to bind the viral protein. Each of these tvb homologs can subsequently be screened for proper folding, e.g., by including an HA epitope or the like. Subsequently, virus-insensitive clones isolated from the combinatorial library can be fused back to C-terminal sequences, and the mutants tested for their ability to confer resistance to ALSV infection or the like while retaining other biological activities of the authentic protein.

The invention also provides for reduction of the tvb protein to generate mimetics, e.g. peptide or non-peptide agents, which are able to disrupt a biological activity of a tvb polypeptide of the present invention, e.g. as inhibitors of protein-protein interactions, such as with TRAF proteins. Likewise, viral proteins can be used to generate peptide mimetics which bind to tvb and inhibit viral infection. Thus, such mutagenic techniques as described above are also useful to map the determinants of the tvb proteins which participate in protein-protein interactions involved in, for example, interaction of the subject tvb polypeptide with TRAFs or other intracellular elements, or with extracellular TNF-like ligands or virus.

To illustrate, the critical residues of a subject tvb polypeptide which are involved in molecular recognition of a TRAF protein can be determined and used to generate tvb-derived peptidomimetics which competitively inhibit binding of the authentic tvb protein with that moiety. By employing, for example, scanning mutagenesis to map the amino acid residues of a protein which is involved in binding other proteins, peptidomimetic compounds can be generated which mimic those residues which facilitate the interaction. Such mimetics may then be used to interfere with the normal function of a tvb protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactamn rings (Garvey et al. in Peptides: Chemistry and Biology, G. R. Marshall ed., ESCOM Publisher: Leiden, Netherlands, 1988), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with a tvb protein. For example, by using immunogens derived from a tvb protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a tvb polypeptide or an antigenic fragment which is capable of eliciting an antibody response). Techniques for conferring immunogenicity on a protein or peptide include conjugation to carriers or other techniques well known in the art. An immunogenic portion of a tvb protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a tvb protein of an organism, such as a mammal, e.g. antigenic determinants of a protein represented by SEQ ID No: 2 or closely related homologs (e.g. at least 70% homologous, preferably at least 80% homologous, and more preferably at least 90% homologous). In yet a further preferred embodiment of the present invention, in order to provide, for example, antibodies which are immuno-selective for discrete tvb homologs the anti-tvb polypeptide antibodies do not substantially cross react (i.e. does not react specifically) with a protein which is, for example, less than 85%, 90% or 95% homologous with the selected tvb. By "not substantially cross react", it is meant that the antibody has a binding affinity for a nonhomologous protein which is at least one order of magnitude, more preferably at least 2 orders of magnitude, and even more preferably at least 3 orders of magnitude less than the binding affinity of the antibody for the intended target tvb.

Following immunization of an animal with an antigenic preparation of a tvb polypeptide, anti-tvb antisera can be obtained and, if desired, polyclonal anti-tvb antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256:495–497), the human B cell hybridoma technique (Kozbar et al., (1983) Immunology Today, 4:72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a tvb polypeptide of the present invention and monoclonal antibodies isolated from a culture comprising such hybridoma cells.

The term antibody as used herein is intended to include fragments thereof which are also specifically reactive with a tvb polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a tvb protein conferred by at least one CDR region of the antibody.

Both monoclonal and polyclonal antibodies (Ab) directed against authentic tvb polypeptides, or tvb variants, and antibody fragments such as Fab, F(ab)$_2$, Fv and scFv can be used to block the action of a tvb protein and allow the study of the role of these proteins in, for example, differentiation of tissue. Experiments of this nature can aid in deciphering the role of tvb proteins that may be involved in control of proliferation versus differentiation, e.g., in patterning and tissue formation.

Antibodies which specifically bind tvb epitopes can also be used in immunohistochemical staining of tissue samples in order to evaluate the abundance and pattern of expression of each of the subject tvb polypeptides. Anti-tvb antibodies can be used diagnostically in immuno-precipitation and immuno-blotting to detect and evaluate tvb protein levels in tissue as part of a clinical testing procedure. For instance, such measurements can be useful in predictive valuations of the onset or progression of proliferative or differentiative disorders. Likewise, the ability to monitor tvb protein levels in an individual can allow determination of the efficacy of a given treatment regimen for an individual afflicted with such a disorder. The level of tvb polypeptides may be measured from cells in bodily fluid, such as in samples of cerebral spinal fluid or amniotic fluid, or can be measured in tissue, such as produced by biopsy. Diagnostic assays using anti-tvb antibodies can include, for example, immunoassays designed to aid in early diagnosis of a disorder, particularly ones which are manifest at birth. Diagnostic assays using anti-tvb polypeptide antibodies can also include immunoassays designed to aid in early diagnosis and phenotyping neoplastic or hyperplastic disorders.

Another application of anti-tvb antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a tvb protein, e.g. orthologs of the tvb protein from other species, can then be detected with antibodies, as, for example, reacting nitrocellulose filters lifted from infected plates with anti-tvb antibodies. Positive phage detected by this assay can then be isolated from the infected plate. Thus, the presence of tvb homologs can be detected and cloned from other animals, as can alternate isoforms (including splicing variants) from humans.

Moreover, the nucleotide sequences determined from the cloning of tvb genes from organisms will further allow for the generation of probes and primers designed for use in identifying and/or cloning tvb homologs in other cell types, e.g. from other tissues, as well as tvb homologs from other organisms. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence selected from the group consisting of SEQ ID No: 1 or naturally occurring mutants thereof. For instance, primers based on the nucleic acid represented in SEQ ID No: 1 can be used in PCR reactions to clone tvb homologs. Likewise, probes based on the subject tvb sequences can be used to detect transcripts or genomic sequences encoding the same or homologous proteins. In preferred embodiments, the probe fuirther comprises a label group attached thereto and able to be detected, e.g. the label group is selected from amongst radioisotopes, fluorescent compounds, enzymes, and enzyme co-factors.

Such probes can also be used as a part of a diagnostic test kit for identifying cells or tissue which misexpress a tvb protein, such as by measuring a level of a tvb-encoding nucleic acid in a sample of cells from a patient-animal; e.g. detecting tvb mRNA levels or determining whether a genomic tvb gene has been mutated or deleted.

To illustrate, nucleotide probes can be generated from the subject tvb genes which facilitate histological screening of intact tissue and tissue samples for the presence (or absence) of tvb-encoding transcripts. Similar to the diagnostic uses of anti-tvb antibodies, the use of probes directed to tvb messages, or to genomic tvb sequences, can be used for both predictive and therapeutic evaluation of allelic mutations which might be manifest in, for example, degenerative disorders marked by apoptosis, neoplastic or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a tvb protein. For instance, variation in polypeptide synthesis can be differentiated from a mutation in a coding sequence.

Accordingly, the present method provides a method for determining if a subject is at risk for a disorder characterized by aberrant apoptosis, cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a tvb-protein, or (ii) the mis-expression of the tvb gene. To illustrate, such genetic lesions can be detected by ascertaining the existence of at least one of (i) a deletion of one or more nucleotides from a tvb gene, (ii) an addition of one or more nucleotides to a tvb gene, (iii) a substitution of one or more nucleotides of a tvb gene, (iv) a gross chromosomal rearrangement of a tvb gene, (v) a gross alteration in the level of a messenger RNA transcript of a tvb gene, (vii) aberrant modification of a tvb gene, such as of the methylation pattern of the genomic DNA, (vii) the presence of a non-wild type splicing pattern of a messenger RNA transcript of a tvb gene, (viii) a non-wild type level of a tvb-protein, and (ix) inappropriate post-translational modification of a tvb-protein. As set out below, the present invention provides a large number of assay techniques for detecting lesions in a tvb gene, and importantly, provides the ability to discern between different molecular causes underlying tvb-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a tvb gene, such as represented by SEQ ID No: 1, or naturally occurring mutants thereof, or 5' or 3' flanking sequences or intronic sequences naturally associated with the subject tvb genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1944) PNAS 91:360–364), the later of which can be particularly useful for detecting point mutations in the tvb gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a tvb gene under conditions such that hybridization and amplification of the tvb gene (if present) occurs, and (iv) detecting the presence or absence of an amplification product, or detecting the size of the amplification product and comparing the length to a control sample.

In still another embodiment, the level of a tvb-protein can be detected by immunoassay. For instance, the cells of a biopsy sample can be lysed, and the level of a tvbprotein present in the cell can be quantitated by standard immunoassay techniques. In yet another exemplary embodiment, aberrant methylation patterns of a tvb gene can be detected by digesting genomic DNA from a patient sample with one or more restriction endonucleases that are sensitive to methylation and for which recognition sites exist in the tvb gene (including in the flanking and intronic sequences). See, for example, Buiting et al. (1994) Human Mol Genet 3:893–895. Digested DNA is separated by gel electrophoresis, and hybridized with probes derived from, for example, genomic or cDNA sequences. The methylation status of the tvb gene can be determined by comparison of the restriction pattern generated from the sample DNA with that for a standard of known methylation.

In still other embodiments, the extracellular domain of the tvb receptor can be used to quantitatively detect the level of tvb ligands, e.g., such as TNF-like molecules which may bind to tvb or viruses such as ALSV. To illustrate, a soluble form of the N-terminus of the receptor can be generated by truncation of the protein prior to the transmembrane domain. Samples of bodily fluid(s), e.g., plasma, serum, lymph, marrow, cerebral/spinal fluid, urine and the like, can be contacted with the receptor under conditions wherein ligand/receptor binding can occur, and the level of ligand/receptor complexes formed can be detected by any of a variety of techniques known in the art. For example, competitive binding assays using standardized samples of a known tvb ligand can be used to quantitate the amount of analyte bound from the fluid sample.

In yet other embodiments, such tvb receptors can be used to detect the presence of a tvb ligand on a cell surface. For instance, the tvb protein can be contacted with cells from a biopsy, and the ability of the tvb protein to decorate certain cells of the sample is ascertained. The binding of the tvb protein to cell populations of the sample can be detected, for example, by the use of antibodies against the tvb protein, or by detection of a label associated with the tvb protein. In the case of the latter, the tvb protein can be labeled, for example, by chemical modification or as a fusion protein. Exemplary labels include radioisotopes, fluorescent compounds, enzyme co-factors, which can be added by chemical modification of the protein, and epitope tags such as myc, pFLAG and the like, or enzymatic activities such as GST or alkaline phosphatase which can be added either by chemical modification or by generation of a fusion protein.

Furthermore, the present invention also contemplates the detection of soluble forms of the tvb receptor in bodily fluid samples. As described in the art, e.g., see Diez-Ruiz et al. (1995) *Eur J Haematol* 54:1–8 and Owen-Schaub et al. (1995) *Cancer Lett* 94:1–8, soluble forms of the TNF-RI and Fas receptors are believed to play a role as modulators of the biological finction of their cognate ligands in an agonist/antagonist pattern. In various pathologic states, the production and release of soluble tvb receptors may mediate host response and determine the course and outcome of disease by interacting with tvb ligands and competing with cell surface receptors. The determination of soluble tvb receptors in body fluids, as with soluble forms of TNF-RI and Fas, is a new tool to gain information about various disease states, and may be of prognostic value to a clinician. For example, the level of soluble tvb protein in a body fluid may give useful information for monitoring, inter alia, cancer, neurodegenerative disorders and/or autoimmune diseases.

The level of soluble receptor present in a given sample can be quantitated, in light of the present disclosure, using known procedures and techniques. For example, antibodies immunoselective for the extracellular domain of the tvb protein can be used to detect and quantify its presence in a sample, e.g., by well-known immunoassay techniques. Alternatively, a labeled ligand of the receptor can be used to detect the presence of the receptor in the fluid sample.

In yet another aspect of the invention, the subject tvb polypeptides can be used to generate a "two hybrid" assay or an "interaction trap" assay (see, for example, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; Iwabuchi et al. (1993) *Oncogene* 8:1693–1696; and Brent WO94/10300), for isolating coding sequences for other cellular proteins which bind tvbs ("tvb-binding proteins" or "tvb-bp"). Such tvb-binding proteins would likely be involved in the regulation of tvb, e.g., as TRAFs or other signal transducers.

Briefly, the interaction trap relies on reconstituting in vivo a functional transcriptional activator protein from two separate fuision proteins. In particular, the method makes use of chimeric genes which express hybrid proteins. To illustrate, a first hybrid gene comprises the coding sequence for a DNA-binding domain of a transcriptional activator fused in frame to the coding sequence for a tvb polypeptide, such as the cytoplasmic domain including the death domains. The second hybrid protein encodes a transcriptional activation domain fused in frame to a sample gene from a cDNA library. If the bait and sample hybrid proteins are able to interact, e.g., form a tvb-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the tvb and sample proteins.

A number of techniques exist in the art for now identifying the ligand of the tvb receptor. For instance, expression cloning can be carried out on a cDNA or genomic library by isolating cells which are decorated with a labeled form of the receptor. In a preferred embodiment, the technique uses the tvb receptor in an in situ assay for detecting tvb ligands, e.g., TNF homologs, in tissue samples and whole organisms. In general, the RAP-in situ assay (for Receptor Affinity Probe) of Flanagan and Leder (see PCT publications WO 92/06220; and also Cheng et al. (1994) *Cell* 79:157–168) involves the use of an expression cloning system whereby a tvb ligand is scored on the basis of binding to a tvb/alkaline phosphatase fusion protein. In general, the method comprises (i) providing a hybrid molecule (the affinity probe) including the tvb receptor, or at least the extracellular domain thereof, covalently bonded to an enzymatically active tag, preferably for which chromogenic substrates exist, (ii) contacting the tissue or organism with the affinity probe to form complexes between the probe and a cognate ligand in the sample, removing unbound probe, and (iii) detecting the affinity complex using a chromogenic substrate for the enzymatic activity associated with the affinity probe.

This method, unlike other prior art methods which are carried out only on dispersed cell cultures, provides a means for probing non-dispersed and wholemount tissue and animal samples. The method can be used, in addition to facilitating the cloning of tvb ligands, also for detecting patterns of expression for particular ligands of the tvb receptor, for measuring the affinity of receptor/ligand interactions in tissue samples, as well as for generating drug screening assays in tissue samples. Moreover, the affinity probe can also be used in diagnostic screening to determine whether a tvb ligand is misexpressed.

Furthermore, by making available purified and recombinant tvb polypeptides, the present invention facilitates the development of assays which can be used to screen for drugs, including tvb homologs, which are either agonists or antagonists of the normal cellular function of the subject tvb receptor, or of its role in the pathogenesis of cellular maintenance, differentiation and/or proliferation and disorders related thereto. Moreover, because we have also identified the function of tvb receptors in viral infectivity, the present invention further provides drug screening assays for detecting agents which inhibit infection by tvb-dependent viruses, e.g., certain ALSV strains and the like. In a general sense, the assay evaluates the ability of a compound to modulate binding between a tvb polypeptide and a molecule, be it derived from a cellular protein or an extracellular protein (ligand agonist or virus), that interacts with the tvb polypeptide. Exemplary compounds which can be screened against such tvb-mediated interactions include peptides, nucleic acids, carbohydrates, small organic molecules, and natural product extract libraries, such as isolated from animals, plants, fungus and/or microbes.

It is contemplated that any of the novel interactions described herein could be exploited in a drug screening assay. For example, in one embodiment, the interaction between a tvb protein and a TRAF can be detected in the presence and the absence of a test compound. The effect of a test compound on the binding of a tvb protein to other molecules, such as cytoskeletal components, or other proteins identified by the tvb-dependent interaction trap assay set out above, could be tested.

In another embodiment, the ability of a compound to modulate the binding of a tvb protein with a viral protein can be assessed. The identification of a test compound which inhibits, for example, tvb-dependent infection by ALSV-B or ALSV-D would be useful in the prevention of such infection in poultry stocks.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include a tvb polypeptide, compound(s) of interest, and a "target polypeptide", e.g., a protein, which interacts with the tvb polypeptide. Exemplary target polypeptides include TRAF proteins and ALSV coat proteins. Detection and quantification of complexes containing the tvb protein provide a means for determining a compound's efficacy at inhibiting (or potentiating) complex formation between the tvb and the target polypeptide. The efficacy of the compound can be assessed by generating dose response curves from data obtained using various concentrations of the test compound. Moreover, a control assay can also be performed to provide a baseline for comparison. In the control assay, isolated and purified tvb polypeptide is added to a composition containing the target polypeptide and the formation of a complex is quantitated in the absence of the test compound.

Complex formation between the tvb polypeptide and the target polypeptide may be detected by a variety of techniques. Modulation of the formation of complexes can be quantitated using, for example, detectably labeled proteins such as radiolabeled, fluorescently labeled, or enzymatically labeled tvb polypeptides, by immunoassay, by chromatographic detection, or by detecting the intrinsic activity of the acetylase.

Typically, it will be desirable to immobilize either tvb or the target polypeptide to facilitate separation of complexes from uncomplexed forms of one or both of the proteins, as well as to accommodate automation of the assay. Binding of tvb to the target polypeptide, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/tvb (GST/tvb) fusion proteins can be adsorbed onto glutathione sepharose beads (Sigma Chemical, St. Louis, Mo.) or glutathione derivatized microtitre plates, which are then combined with the cell lysates, e.g. an $^{35}S$-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of tvb-binding protein found in the bead fraction quantitated from the gel using standard electrophoretic techniques such as described in the appended examples.

Other techniques for immobilizing proteins on matrices are also available for use in the subject assay. For instance, either tvb or target polypeptide can be immobilized utilizing conjugation of biotin and streptavidin. For instance, biotinylated tvb molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with tvb, but which do not interfere with the interaction between the tvb and target polypeptide, can be derivatized to the wells of the plate, and tvb trapped in the wells by antibody conjugation. As above, preparations of an target polypeptide and a test compound are incubated in the tvb-presenting wells of the plate, and the amount of complex trapped in the well can be quantitated. Exemplary methods for detecting such complexes, in addition to those described above for the GST-immobilized complexes, include immunodetection of complexes using antibodies reactive with the target polypeptide, or which are reactive with tvb protein and compete with the target polypeptide; as well as enzyme-linked assays which rely on detecting an enzymatic activity associated with the target polypeptide, either intrinsic or extrinsic activity. In the instance of the latter, the enzyme can be chemically conjugated or provided as a fusion protein with the target polypeptide. To illustrate, the target polypeptide can be chemically cross-linked or genetically fused with horseradish peroxidase, and the amount of polypeptide trapped in the complex can be assessed with a chromogenic substrate of the enzyme, e.g. 3,3'-diamino-benzidine tetrahydrochloride or 4-chloro-1-naphthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating proteins trapped in the complex, antibodies against the protein, such as anti-tvb antibodies, can be used. Alternatively, the protein to be detected in the complex can be "epitope tagged" in the form of a fusion protein which includes, in addition to the tvb sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, N.J.).

In another embodiment of a drug screening, a two hybrid assay (described supra) can be generated with a tvb and tvb-binding protein. Drug dependent inhibition or potentiation of the interaction can be scored.

Furthermore, each of the assay systems set out above can be generated in a "differential" format. That is, the assay format can provide information regarding specificity as well as potency. For instance, side-by-side comparison of a test compound's effect on different complexes between TRAFs and various members of the TNF receptor superfamily can provide information on selectivity, and permit the identification of, for example, compounds which selectively modulate the bioactivity of only tvb-dependent complexes.

In yet another embodiment, the drug screening assay is derived to include a whole cell recombinantly expressing a tvb polypeptide. The ability of a test agent to alter the activity of the tvb protein can be detected by analysis of the recombinant cell. For example, agonists and antagonists of the tvb biological activity can by detected by scoring for alterations in apoptosis, growth or differentiation (phenotype) of the cell. General techniques for detecting each are well known, and will vary with respect to the source of the particular reagent cell utilized in any given assay.

In an exemplary embodiment, a cell which expresses the tvb receptor, e.g, whether endogenous or heterologous, can be contacted with a ligand of the tvb receptor which is capable of inducing signal transduction from the receptor, and the resulting signaling detected either at various points in the pathway, or on the basis of a phenotypic change to the reagent cell. In one embodiment, the reagent cell is contacted with an imnmunoadhesion molecule (described in the appended examples) comprising the subgroup B RAV-2 SU envelope protein fused to the constant regions of an immunoglobulin, and the apoptotic signal cascade induced by that construct is subsequently detected. A test compound which modulates that pathway, e.g., potentiates or inhibits, can be detected by comparison with control experiments which either lack the receptor or lack the test compound.

For example, there are a variety of techniques available in the art for detecting the effects of a test compound on rescuing the apoptotic cell of the present invention. For instance, the level of apoptosis can be assessed by measuring cellular DNA fragmentation, such as by detection of nucleosomal-length DNA fragments on agarose electrophoretic gels (see e.g., Quingsheng et al. (1991) Cell 67:629–639). Other suitable assays of apoptosis include uptake of Hoechst 33342 dye (see e.g., Hardin et al. (1992) J. Immunol. Methods 154:99–107), detection of nuclear DNA damage using the intercalating dye p-phenylenediamine (see e.g., Salcedo et al. (1992) J. Immunol. Methods 148:209–216) and flow cytometry assays as described in Darzynkiewicz, Z. et al. (1992) Cytometry 13:795–808. Additionally, visual inspection of the morphology of the reagent cell can be used to determine whether the biological activity of the targeted tvb protein has been affected by the added agent. To illustrate, the ability of an agent to influence an apoptotic phenotype can be assessed by visual microscopy. Likewise, the formation of certain cellular structures as part of differentiation, such as the formation of neuritic process, can be visualized under a light microscope.

Thus, as an illustration of the subject assay in practice, agents able to modulate tvb-mediated apoptosis can be identified by the steps of (i) providing a population of test cells comprising a tvb (optionally recombinant) gene, which gene is expressible to levels in the cell which can cause apoptosis upon receptor cross-linking; (ii) contacting the test cell population with a candidate agent under conditions wherein the recombinant tvb gene is expressed and inducing apoptosis; (iii) determining the amount of cell death in the presence of the candidate agent; and (iv) comparing the amount of cell death in the presence of the candidate agent to an amount of cell death occurring in the absence of the candidate agent. A statistically significant change in the level of cell death occurring in the presence of the candidate agent is indicative of an agent which modulates tvb-mediated apoptosis. Agents can thus be tested for their ability to act as tvb inhibitors or potentiators of apoptosis In yet another embodiment, rather than detect cell death per se, the assay can be enerated to evolve a detection signal from the expression or modification of a cellular protein effected by the activation of apoptotic mechanisms through activation of tvb-mediated signaling. Such indirect measurement of activation of the apoptotic pathway by tvb overexpression can be accomplished by detecting a biological activity modulated by the downstream effects of the receptor activity. One apoptotic pathway which is likely to be induced by tvb overexpression, based on TNF receptor data, is a p53-dependent pathway. Accordingly, a variety of techniques can be employed to detect the upregulated response of p53 in the recombinant tvb cell, or of another downstream target of tvb activation.

For example, the level of p53 can be detected directly, such as by immunoassay techniques (including immunoprecipitation/SDS-PAGE) using anti-p53 antibodies (e.g., anti-p53 (human) antibody is available as PharMingen catalog Nos. 14091A and 14211A). In an exemplary assay, fibroblast expressing the tvb receptor are, under apoptotic conditions, contacted with a test agent, harvested, and lysed by standard techniques. The p53 protein levels in the cell sample are determined by immunoassay, and compared against p53 levels in untreated cells.

However, it will be clear to those skilled in the art that the use of antibodies in these assays is merely illustrative of binding molecules in general, and that the antibodies are readily substituted in the assay with any suitable molecule that can specifically detect p53. To further illustrate, certain of the natural binding partners of p53 can be used in place of an antibody to detect the presence of p53 in a cell. For example, the proteins MDM2 (Barak et al. (1992) EMBO J 11:2115; and Oliner et al. (1992) Nature 358:80) or WBP1 (Bischoff et al. PCT publication WO95/14777) can be substituted as p53-binding molecules for quantitating the level of p53 in a cell sample.

In yet an another embodiment of the subject assay, the means for detecting p53 comprises, for example, a reporter gene construct which includes a transcriptional regulatory element which binds and is responsive to the p53 protein. The gene product is a detectable label, the signal from which is dependent in dose-dependent manner on the level of p53 in the cell. Exemplary reporter genes include enzymes, such as luciferase or β-galactosidase which can produce a spectrometrically active label, or a gene product which alters a cellular phenotype, e.g., drug resistance or auxotrophy.

An exemplary reporter gene construct comprises a luciferase gene whose expression is driven by the core Herpes simplex virus thymidine-kinase (TK) promoter which has been modified with a p53 responsive element (p53RE/TK). See, for example, U.S. Pat. No. 5,362,623. When a version of the construct lacking any of the modifications to the TK promoter is transfected into mammalian cells, the detectable luciferase activity is low because this core TK promoter fragment does not contain the upstream activating sequences necessary for efficient transcriptional activation of the luciferase gene. However transfection with the constructs in which TK is further modified to contain either 3 or 6 response-elements (RE) for p53, the detectable luciferase activity increases in cells in a dose-dependent manner relative to p53 levels.

The p53RE/TK vector is transfected into a p53$^+$ cell-line which is capable of undergoing apoptosis in a manner mediated by an endogenous or exogenous tvb receptor. Luciferase expression is upregulated by the presence of p53, which functions as a transcriptional activating factor by binding to the p53 response element upstream of the TK promoter. Measurement of luciferase activity can be carried out by standard protocols (see, for example, Promega Technical Bulletin #TB161). Cells are grown and transfected in a tissue culture grade 96 well microtitre plate. The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay substrate (Beetle luciferin, Promega catalog no. E1603) is added, and the reaction in each well monitored in a luminometer or scintillation counter. Upregulation of the p53 system results in a greater luminescence signal than the uninduced system. A salient feature of this assay is that, although it is an in vivo assay, this screen will ignore general cytotoxic compounds.

As an illustration of the subject assay in practice, agents able to modulate tvb-mediated apoptosis can be identified by the steps of (i) providing a population of test cells comprising a recombinant tvb receptor gene, and a reporter gene under transcriptional control of a p53 responsive element; (ii) contacting the cell with a candidate agent under conditions wherein the recombinant tvb gene is expressed and apoptosis occurs in a tvb-dependent manner; (iii) detecting the level of expression of the reporter gene; and (iv) comparing the measured level of reporter gene expression in the presence of the candidate agent with a level of expression in the absence of the candidate agent. A statistically significant decrease in level of expression of the reporter gene, relative to a level of expression in the absence of the candidate agent, is indicative of an agent which inhibits tvb-mediated apoptosis.

In yet another embodiment, the alteration of expression of a reporter gene construct provided in the reagent cell provides a means of detecting the effect on tvb activity. For example, reporter gene constructs derived using the transcriptional regulatory sequences, e.g. the promoters, for developmentally regulated genes can be used to drive the expression of a detectable marker, such as a luciferase gene. In an illustrative embodiment, the construct is derived using the promoter sequence from a NF-κB gene which regulates expression of a reporter gene. See, for example, Schindler et al. (1994) *Mol Cell Biol* 14:5820–5831.

Many reporter genes are known to those of skill in the art and others may be identified or synthesized by methods known to those of skill in the art. A reporter gene includes any gene that expresses a detectable gene product, which may be RNA or protein. Preferred eporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282:864–869) and include other enzyme detection systems, such as beta-galactosidase; firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667); alkaline phosphatase (Toh et al. (1989) Eur. J. Biochem. 182:231–238, Hall et al. (1983) J. Mol. Appl. Gen. 2:101); and human placental secreted alkaline phosphatase (Cullen and Malim (1992) Methods in Enzymol. 216:362–368).

In still other embodiments, the signal generated by engagement of the tvb receptor can be detected by scoring for the production of second messengers. For example, in various embodiments the assay may assess the ability of test agent to cause changes in phophorylation patterns, adenylate cyclase activity (cAMP production), GTP hydrolysis, calcium mobilization, and/or phospholipid hydrolysis upon receptor stimulation.

In yet another embodiment, the cell-based assay can be used to detect agents which inhibit the viral infectivity of a tvb expressing cell. In general, the assay can make use of the ability of a recombinant virus to deliver a reporter gene to a cell expressing the tvb protein, with the level of infection at least semi-quantifiable by detecting the level of virus-conferred reporter gene. Agents which inhibit viral infection can be detected by monitoring the percent population of cells which express the reporter gene. In an illustrative embodiment, an recombinant ALSV can be engineered to include a reporter gene, and the infectivity of the virus in the presence of a test agent compared to that in the absence of the test agent and/or absence of the test compound.

In other embodiments, test agents having potential antiviral activity can be identified in an assay which provides simply detects the binding of viral particles or coat proteins thereof to the tvb receptor. For instance, cells can be engineered to express a tvb receptor, preferably a truncated receptor which retains the extracellular domain but which is not competent to transduce intracellular signals, e.g., does not cause apoptosis upon ligand engagement. The level of virus/virus protein bound to the tvb receptor can be assessed, for example, by detection of a labeled viral protein, by immunoassay using antibodies against a viral protein, or by detection of a labeled competitive ligand. In a preferred embodiment, the viral protein is decorated with a fluorescent label, e.g., by use of a fluorescein-conjugated antibody or the like, and the level of labeling of the cells detected by FACS analysis in the presence and absence of the test agent.

Another aspect of the present invention relates to a method of inducing and/or maintaining a differentiated state, enhancing survival, and/or inhibiting (or alternatively potentiating) proliferation of a cell, by contacting the cells with an agent which modulates tvb-dependent signal transduction pathways. For instance, it is contemplated by the invention that, in light of the present finding of an apparently broad involvement of proteins of the TNF superfamily in the control of apoptosis, proliferation and/or differentiation, the subject method could be used to generate and/or maintain an array of different tissue both in vitro and in vivo. A "tvb therapeutic," whether inhibitory or potentiating with respect to modulating signaling by the tvb receptor, can be, as appropriate, any of the preparations described above, including isolated polypeptides, gene therapy constructs, antisense molecules, peptidomimetics or agents identified in the drug assays provided herein.

In yet another embodiment, soluble forms of the tvb protein including the extracellular ligand-binding domain of the receptor can be provided as a means for antagonizing the binding of a tvb ligand to a cell-surface tvb receptor. For instance, such forms of the receptor can be used to antagonize the bioactivity of a ligand of the TNF superfamily. In other embodiments, the soluble receptor formulation can be used to inhibit viral infection by competitively binding and sequestering viral particles. For instance, such formulations may be used to prevent infection of avian stocks by certain ALSV sub-types, or prevent infection of mammalian cells by, for example, FeLV or the like.

As described by Wallach et al. U.S. Pat. No. 5,478,925, TNF-RI monomers must be administered in very high doses in order to result in effective inhibition of TNF-binding to cells in the human body. The multimers of the soluble forms of TNF-RI, according to Wallach et al., are understood to be more effective in inhibiting TNF activity at lower doses, since they can effectively compete with the TNF trimers for the binding sites on the aggregates of the cell surface TNF-RIs.

Accordingly, in a preferred embodiment, formulations of multimeric tvb receptors are provided. The multimers of the soluble forms of the subject tvb receptors may be produced according to the methods of Wallach et al. In one embodiment, the tvb multimers are crosslinked chemically by using known methods which will result in the formation of either dimers or higher multimers of the soluble forms of the tvb receptor. Another way of producing the multimers of the soluble forms of the tvb receptor is by recombinant techniques, e.g., by inclusion of hinge regions. This linker can facilitate enhanced flexibility of the chimeric protein allowing the various tvb monomeric subunits to freely and (optionally) simultaneously interact with a tvb ligand by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

The tvb multimers of the present invention have the ability to interfere with the binding of a tvb ligand to its receptors and/or to block the effects of that ligand. Each multimer comprises two or more monomers, each comprising the soluble form of a tvb receptor or a salt or functional derivative thereof. The upper limit for the number of monomers in a multimer is not important and liposomes having many such monomers thereon may be used. Such multimers preferably have 2–5 monomers and more preferably 2 or 3.

The tvb compounds of the present invention are likely to play an important role in the modulation of cellular proliferation. There are a wide variety of pathological cell proliferative conditions for which tvb therapeutics of the present invention may be used in treatment. For instance, such agents can provide therapeutic benefits where the general strategy being the inhibition of an anomalous cell proliferation. Diseases that might benefit from this methodology include, but are not limited to various cancers and leukemias, psoriasis, bone diseases, fibroproliferative disorders such as involving connective tissues, atherosclerosis and other smooth muscle proliferative disorders, as well as chronic inflammation.

The apoptosis regulating compositions and methods of this invention can regulate or control apoptosis in the treatment of, for example, retrovirus-related disease including AIDS, ARC (AIDS related complex), ATL (adult T cell leukemia), hairy cell leukemia, myelopathy (HAM/TSP), respiratory disorder (HAB/HABA), arthropathy (HAAP), HIV- or HTLV-I (human T cell leukemia virus type I)-related diseases such as uveitis (HAU), and C-type hepatitis; autoimmune diseases including collagen diseases such as SLE (systemic lupus erythematosus) and rheumatoid arthritis (RA), ulcerative colitis, Sjogren's syndrome, primary biliary hepatic cirrhosis, idiopathic thrombocytopenic purpura (ITP), autoimmune hemolytic anemia, myasthenia gravis, Hashimoto's disease and insulin dependent (type I) diabetes mellitus; diseases accompanied by thrombocytopenia, for example, myelodysplastic syndrome (MDS), periodic thrombocytopenia, aplastic anemia, idiopathic thrombocytopenia and disseminated intravascular coagulation; liver diseases such as viral or drug-induced hepatitis (such as types C, A, B, and F) and hepatic cirrhosis; neurodegenerative disorders, such as Alzheimer's disease (AD), Huntington's disease (HD) and Parkinson's disease; myocarditis; ARDS (adult respiratory distress syndrome); infectious diseases; prostatic hypertrophy; uterine myoma; bronchial asthma; arteriosclerosis; congenital malformations; nephritis; senile cataract; chronic fatigue syndrome (CFS); and myotonic dystrophy.

In addition, the present invention contemplates the use of tvb therapeutics for the treatment of differentiative disorders which result from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be apparent that, by transient use of modulators of tvb activities, in vivo reformation of tissue can be accomplished, e.g. in the development and maintenance of organs. By controlling the proliferative and differentiative potential for different cells, the subject tvb therapeutics can be used to reform injured tissue, or to improve grafting and morphology of transplanted tissue. For instance, tvb antagonists and agonists can be employed in a differential manner to regulate different stages of organ repair after physical, chemical or pathological insult. For example, such regimens can be utilized in repair of cartilage, increasing bone density, liver repair subsequent to a partial hepatectomy, or to promote regeneration of lung tissue in the treatment of emphysema. The present method is also applicable to cell culture techniques.

In one embodiment, the tvb therapeutic of the present invention can be used to induce differentiation of uncommitted progenitor cells and thereby give rise to a committed progenitor cell, or to cause further restriction of the developmental fate of a committed progenitor cell towards becoming a terminally-differentiated cell. For example, the present method can be used in vitro or in vivo to induce and/or maintain the differentiation of hematopoietic cells into erythrocytes and other cells of the hematopoietic system. In an illustrative embodiment, the effect of erythropoietin (EPO) on the growth of EPO-responsive erythroid precursor cells is increased to influence their differentiation into red blood cells. For example, as a result of administering an inhibitor of histone deacetylation, the amount of EPO, or other differentiating agent, required for growth and/or differentiation is reduced (PCT/US92/07737). Accordingly, the tvb therapeutics of the present invention, particularly those which antagonize tvb deacetylase activity, can be administered alone or in conjunction with EPO and in a suitable carrier to vertebrates to promote erythropoiesis. Alternatively, cells could be treated ex vivo. Such treatment is contemplated in the treatment of a variety of disease states, including in individuals who require bone marrow transplants (e.g. patients with aplastic anemia, acute leukemias, recurrent lymphomas, or solid tumors).

To illustrate, prior to receiving a bone marrow transplant, a recipient is prepared by ablating or removing endogenous hematopoietic stem cells. Such treatment is usually carried out by total body irradiation or delivery of a high dose of an alkylating agent or other chemotherapeutic, cytotoxic agent (Anklesaria, et al. (1987) *PNAS* 84:7681–7685). Following preparation of the recipient, donor bone marrow cells are injected intravenously. Optionally, the tvb therapeutics of the present invention could be contacted with the cells ex vivo or administered to the subject with the reimplanted cells.

Yet another aspect of the present invention concerns the application of tvb therapeutics to modulating morphogenic signals involved in organogenic pathways. Thus, it is contemplated by the invention that compositions comprising tvb therapeutics can also be utilized for both cell culture and therapeutic methods involving generation and maintenance of tissue.

Another aspect of the invention features transgenic non-human animals which express a heterologous tvb gene of the present invention, and/or which have had one or more genomic tvb genes disrupted in at least a tissue or cell-types of the animal. Accordingly, the invention features an animal model for developmental diseases, which animal has one or more tvb allele which is mis-expressed. For example, an animal can be generated which has one or more tvb alleles deleted or otherwise rendered inactive. Such a model can then be used to study disorders arising from mis-expressed tvb genes, as well as for evaluating potential therapies for similar disorders.

The transgenic animals of the present invention can be engineered to be resistant to certain viral infection. For instance, chickens or other birds can be engineered such that their endogenous tvb receptor is replaced with a mutant tvb receptor which is characterized by reduced binding affinity for one or more ALSV sub-types, e.g., sub-type B or D viruses.

In another embodiment, the tvb transgene can be provided in an organism's tissue and exploited as a means for tissue-specific gene targeting. ALSVs have been used extensively as genetic vectors in avian systems, but their utility in mammals or mammalian cell lines is compromised by inefficient viral entry. This limitation can be overcome by generating transgenic mammals (non-human) that express the tvb receptor under the control, preferably under the control of a tissue-dependent and/or developmentally-regulated transcriptional regulatory sequence. The cells of the resulting transgenic animals which express the tvb transgene are susceptible to efficient infection by subgroup B ALSV, as described in the appended examples (see also Federspiel et al. (1994) *PNAS* 91:11241–11245). Because infection is restricted to cell lineages that express the transgene, the method has utility for studies of development, oncogenesis, and the like, and will provide models for tissue-specific gene therapy.

The transgenic animals of the present invention all include within a plurality of their cells a transgene of the present invention, which transgene alters the phenotype of the "host cell" with respect to regulation by the tvb receptor, e.g., of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below. Salter, et al. (1987) "Transgenic Chickens: Insertion of Retroviral Genes into the Chicken Germ line" *Virology* 157:236–240; the Bosselman et al. U.S. Pat. No. 5,162,215, entitled "Method of gene transfer into chickens and other avian species";

In one embodiment, the transgene construct is a knockout construct. Such transgene constructs usually are insertion-type or replacement-type constructs (Hasty et al. (1991) *Mol Cell Biol* 11:4509). The transgene constructs for disruption of a tvb gene are designed to facilitate homologous recombination with a portion of the genomic tvb gene so as to prevent the functional expression of the endogenous tvb gene. In preferred embodiments, the nucleotide sequence used as the knockout construct can be comprised of (1) DNA from some portion of the endogenous tvb gene (exon sequence, intron sequence, promoter sequences, etc.) which direct recombination and (2) a marker sequence which is used to detect the presence of the knockout construct in the cell. The knockout construct is inserted into a cell, and integrates with the genomic DNA of the cell in such a position so as to prevent or interrupt transcription of the native tvb gene. Such insertion can occur by homologous recombination, i.e., regions of the knockout construct that are homologous to the endogenous tvb gene sequence hybridize to the genomic DNA and recombine with the genomic sequences so that the construct is incorporated into the corresponding position of the genomic DNA. The knockout construct can comprise (1) a full or partial sequence of one or more exons and/or introns of the tvb gene to be disrupted, (2) sequences which flank the 5' and 3' ends of the coding sequence of the tvb gene, or (3) a combination thereof.

A preferred knockout construct will delete, by targeted homologous recombination, essential structural elements of an endogenous tvb gene. For example, the targeting construct can recombine with the genomic tvb gene can delete a portion of the coding sequence, and/or essential transcriptional regulatory sequences of the gene.

Alternatively, the knockout construct can be used to interrupt essential structural and/or regulatory elements of an endogenous tvb gene by targeted insertion of a polynucleotide sequence. For instance, a knockout construct can recombine with a tvb gene and insert a nonhomologous sequence, such as a neo expression cassette, into a structural element (e.g., an exon) and/or regulatory element (e.g., enhancer, promoter, intron splice site, polyadenylation site, etc.) to yield a targeted tvb allele having an insertional disruption. The inserted nucleic acid can range in size from 1 nucleotide (e.g., to produce a frameshift) to several kilobases or more, and is limited only by the efficiency of the targeting technique.

Depending of the location and characteristics of the disruption, the transgene construct can be used to generate a transgenic animal in which substantially all expression of the targeted tvb gene is inhibited in at least a portion of the animal's cells. If only regulatory elements are targeted, some low-level expression of the targeted gene may occur (i.e., the targeted allele is "leaky").

The nucleotide sequence(s) comprising the knockout construct(s) can be obtained using methods well known in the art. Such methods include, for example, screening genomic libraries with tvb cDNA probes in order to identify the corresponding genomic tvb gene and regulatory sequences. Alternatively, where the cDNA sequence is to be used as part of the knockout construct, the cDNA may be obtained by screening a cDNA library as set out above.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from excised tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A preferred embodiment for introducing a replication-defective retroviral vector into a pluripotent stem cell of an unincubated chick embryo, includes the steps of: (a) making an opening in an unincubated chicken egg containing an embryo to expose a blastoderm; (b) microinjecting through the opening a solution containing the replication-defective retroviral vector into an area around and in close proximity to the blastoderm; and (c) sealing the opening after microinjection.

This procedure is preferably carried out as follows: the chicken egg is an unincubated day old egg; the opening in the egg is approximately equal to 5 mm. in diameter; the microinjection of a solution of vector in a volume of about 5–20 μL is accomplished with a drawn glass needle approximately equal to 40–60 μM outer diameter; and the egg is sealed with membrane from a donor egg and with glue or paraffin.

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83:9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting the tvb gene in ES cells, these changes can be introduced into the germlines of animals to generate chimeras. The gene targeting procedure is accomplished by introducing into tissue culture cells a DNA targeting construct that includes a segment homologous to a tvb locus, and which also includes an intended sequence modification to the tvb genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a tvb gene function through the use of a targeting transgene construct designed to undergo homologous recombination with tvb genomic sequences. Targeting construct can be arranged so that, upon recombination with an element of a tvb gene, a positive selection marker is inserted into (or replaces) coding sequences of the targeted tvb gene. The inserted sequence functionally disrupts the tvb gene, while also providing a positive selection trait.

Generally, the embryonic stem cells (ES cells) used to produce the knockout animals will be of the same species as the knockout animal to be generated. Thus for example, chicken embryonic stem cells will usually be used for generation of a tvb-knockout chicken.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence. Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the tvb coding sequence, transcriptional regulatory sequence, etc. Typically, less than about 1–5 percent of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent.

Offspring that are born to the foster mother may be screened initially for tvb disruptants, DNA from tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from animals that are the product of this cross, as well as animals that are known heterozygotes and wild type animals.

Other means of identifying and characterizing the knockout offspring are available. For example, Northern blots can be used to probe the mRNA for the presence or absence of transcripts of either the tvb gene, the marker gene, or both. In addition, Western blots can be used to assess the (loss of) level of expression of the tvb gene knocked out in various tissues of the offspring by probing the Western blot with an antibody against the tvb protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies or tvb ligands to look for the presence or absence of the knockout construct gene product.

Animals containing more than one knockout construct and/or more than one transgene expression construct are prepared in any of several ways. The preferred manner of preparation is to generate a series of animals, each containing a desired transgenic phenotype. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s). Thus, a transgenic avian species can be generated by breeding a first transgenic bird in which the wild-type tvb gene is disrupted with a second transgenic bird which has been engineered to express a mutant tvb which retains most other biological functions of the receptor except for ALSV binding.

The transformed animals, their progeny, and cell lines of the present invention provide several important uses that will be readily apparent to one of ordinary skill in the art.

To illustrate, the transgenic animals and cell lines are particularly useful in screening compounds that have potential as prophylactic or therapeutic treatments of diseases such as may involve aberrant expression, or loss, of a tvb gene, or aberrant or unwanted activation of receptor signaling. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

EXEMPLICATION

The invention, now being generally described, will be more readily understood by reference to the following examples, which are included merely for purposes of illustration of certain aspects and embodiments of the present invention and are not intended to limit the invention.

ALSV-receptor interactions are a very attractive model system to study retroviral entry because different subgroups of these viruses are predicted to use different genetically-defined cellular receptors. The ALSV family consists of six major subgroups in chickens (designated A to E, and J: Weiss R. A. (1992). Cellular receptors and viral glycoproteins involved in retrovirus entry. In J. A. Levy (Ed.), The Retroviruses, Plenum Press.) Viruses within each subgroup encode immunologically-related Env glycoproteins, and demonstrate cross-interference because they are predicted to use the same cellular receptor (Duff R. G. and Vogt, P. K. (1969) *Virology* 39:18–30, Hanafusa H. (1965) *Virology* 25:248–255, Ishizaki R. and Vogt P. K. (1966) *Virology* 30:375–87, Payne L. N. and Biggs P. M. (1966) *Virology* 29:190–8, Vogt P. and Ishizaki R. (1965) *Virology* 26:664–672, Vogt P. K. (1965) *Virology* 25:237–247). Characterizing different ALSV-receptor interactions might lead to the identification of common principles which govern the mechanisms of retroviral entry into cells.

ALSV subgroup specificity operates at the level of viral entry and is determined by the amino acid sequence of the SU glycoprotein (Dorner A. J. and Coffin J. M. (1986) *Cell* 45:365–74, Bova C. A., et al. (1986) *Virology* 152:343–54, Bova C. A., et al. (1988) *J. Virol.* 63:111–21) The ALSV SU glycoprotein is approximately 350 amino acids in length (Weiss, supra). Previous analysis of molecular recombinants between the SU proteins of viruses representing subgroups B, C, and E, demonstrated that the major subgroup-determining region is contained between amino acid residues 137 and 271 (Dorner, supra). Three variable segments of this region, designated hr1 (amino acids 137–167); hr2 (amino acids 202 to 229); and vr3 (amino acids 260 to 271), governed viral subgroup specificity. The hr1 and hr2 regions were shown to be the major determinants of viral tropism (Dorner, supra). However, amino acid sequences in the vr3 region were found to influence the choice of receptor used. For example, a recombinant Env protein with the subgroup B vr3 region combined with the subgroup B hr1 and subgroup E hr2 regions, gave rise to a virus that used both subgroup B and subgroup E receptors (Dorner, supra). However, a similar recombinant Env protein with the vr3 region derived from a subgroup E virus, only interacted with the subgroup E receptor (Dorner, supra). Because amino acid residues 137 to 271 of ALSV-B, -C, and -E, SU glycoproteins govern viral subgroup specificity, these regions are assumed to contain the sites of receptor interaction (Bova (1986) supra, Dorner supra, Bova (1988) supra). However, the precise receptor-interaction determinants on Env have not been defined for any subgroup of ALSV. The cloning of the subtype B/D receptor, described below, will lead to the identification of important receptor-interaction determinants of ALSV-B Env. Identifying these important residues of Env is crucial for understanding how these viruses recognize and infect target cells.

Chickens are classified based on their susceptibility to infection by different ALSV subgroups e.g. chickens designated C/O are susceptible to ALSV-A, -B, -C, -D, and -E, whereas those designated C/AB are resistant to infection by subgroup-A, and -B viruses (Vogt and Ishizaki, supra). Genetic studies in chickens identified three different autosomal loci, designated tva, tvb, and tvc, which governed susceptibility to infection by viral subgroups -A, -B, and -C, respectively (Crittenden L. B., et al. (1967) *J. Virol.* 1:898–904, Payne L. N. and Biggs P. M. (1964) *Virology* 24:610–616, Payne L. N. and Biggs, P. M. (1966) *Virology* 29:190–8., Payne L. N. and Pani P. K. (1971) *J. Gen. Virol.* 13:253–9, Rubin H. (1965) *Virology* 26:270–276). Distinct alleles at each locus confer susceptibility, or resistance, to viral infection, and the susceptibility alleles are dominant (Weiss, supra). The susceptibility alleles are presumed to encode subgroup-specific ALSV receptors, and the resistance alleles are thought to be defective for this function. The tva and tvc loci are genetically-linked, suggesting that they may be related by a common gene duplication event (Payne (1971) supra). The tvb locus is not linked to tva and tvc. However, viral subgroups B, D, and E exhibit receptor cross-interference, indicating that they might share a common receptor encoded at tvb (Weiss, supra).

Previous genetic studies in chickens demonstrated that ALSV-B, ALSV-D, and ALSV-E most probably use similar or identical receptors encoded by the tvb locus (reviewed in Weiss supra). To date, five different alleles at tvb have been described, conferring three different patterns of susceptibility to these viral subgroups: three alleles ($tvb^{s1}$, $tvb^{s2a}$, and $tvb^{s2b}$ permit infection by all three subgroups; one allele ($tvb^{s3}$) allows infection by viruses of B and D, but not E, subgroups; one allele ($tvb^r$) does not permit entry by any of the three viral subgroups. Receptor-interference studies also support the proposition that these viral subgroups share a common receptor. Preinfection of cells by ALSV-B, or ALSV-D, leads to a block to superinfection by all three viral subgroups. However, preinfection of cells by ALSV-E only blocks superinfection by subgroup E viruses (Weiss supra). This non-reciprocal receptor interference has at least two possible explanations. First, tvb might encode a single receptor for the three viral subgroups, but the receptor might have a higher affinity for the Env glycoproteins of subgroup B and D viruses than for those of subgroup E. Thus, ALSV-B and ALSV-D might infect cells already infected by ALSV-E, by displacing subgroup E Env proteins bound to the common putative receptor (Weiss supra). Second, there might be two tightly linked ALSV receptor genes at tvb: one encoding a receptor for viral subgroups B and D, and the other encoding a receptor for all three viral subgroups (Weiss supra). In this model, preinfection of cells by ALSV-B or ALSV-D, would interfere with both putative receptors, whereas only one receptor would be blocked by ALSV-E infection.

The products of tvb are also of interest, because subgroup-B and subgroup-D viral infection of CEFs often leads to cell-killing (Weller S. K., et al. (1980) *J. Virol.* 33:494–506, Weller S. K. and Temin H. M. (1981) *J. Virol.* 39:713–21.) This cytopathic effect is linked to the same determinants of subgroup B Env that also specify usage of the putative tvb receptor (Dorner supra). Cell death in this system occurs during the acute phase of infection (within the first two to four days, leading to a 30% to 40% reduction in the numbers of viable cells (Weller (1980) supra, Weller (1981) supra). By approximately the tenth day of infection, the surviving chronically-infected viral producer cells continue to grow at the same rate as cells infected by non-cytopathic ALSV subgroups (Weller (1980) supra, Weller (1981) supra). The dead cells contain large amounts of unintegrated viral DNA suggesting that cell-killing might be due to massive levels of viral superinfection. In support of this idea, prevention of viral superinfection, by addition of neutralizing antisera to cultures of CEFs infected by cytopathic subgroups of ALSV, led to a significant reduction in both the cytopathic effect and the amounts of unintegrated viral DNA (Weller (1980) supra, Weller (1981) supra).

There are several important reasons for isolating and characterizing the products of tvb. First, these studies should allow determination of the precise relationship between cellular receptors for viral subgroups B, D, and E, and to establish the molecular details of the entry mechanisms used by these viruses. This information, combined with our knowledge of ALSV-A/tva interactions, should allow us to determine if there are general principles that underlie the process of ALSV entry into cells. Second, by characterizing the interactions between the products of tvb, and the Env glycoproteins of viral subgroups B, and D, we expect to gain a substantial insight into the mechanism(s) of cell-killing induced by these viral infections. Given the importance of this locus, we used a gene transfer approach to isolate a chicken gene with the properties expected of $tvb^{s3}$. Expression of this gene renders mouse NIH 3T3 cells susceptible to infection specifically by ALSV subgroups B and D. A functional cDNA clone derived from this gene encodes a protein with significant similarity to the TNFR/Fas protein family, raising the interesting possibility that this protein participates in virus-associated cell death (as discussed below).

A gene transfer approach, similar to that used successfully to isolate tva (Young J. A. T., et al. (1993) *J. Virol.* 67:1811–1816, Bates P., et al. (1993) *Cell* 74:1043–1051), was used in an attempt to isolate the chicken tvb$^{s3}$ locus, predicted to encode cellular receptors for ALSV-B and -D. Approximately 6×10$^6$ mouse 3T3 cells were co-transfected with 120 µg genomic DNA prepared from C/E CEFs (sheared to an average size of approximately 20 kb), and 12 µg of pMPHis plasmid DNA conferring resistance to histidinol. C/E cells are permissive for infection by viral subgroups -B and -D, but not -E, and thus contain the tvb$^{s3}$ allele. Mouse cells were chosen as recipients for transfection because they are highly resistant to infection by ALSV-B (Bova (1988) supra). However, these cells, like a number of other mammalian cell lines, permit low levels of entry by ALSV-D (Bova (1988) supra).

After transfection, the cells were selected in histidine-free medium containing 1 mM histidinol, a procedure which gave rise to approximately 3,300 individual primary transfectants. In an attempt to determine whether any of these cells had taken up the tvb$^{s3}$ locus, the transfectants were challenged with 6×10$^5$ infectious units of a subgroup B-specific virus, RCASH-B, containing a gene conferring resistance to hygromycin B. This virus was virtually identical to the subgroup A-specific virus RCASH-A (Young supra), except that the subgroup-determining regions were derived from the RAV-2 viral strain (Brojatsch, J., and Young, J. A. T.; unpublished). Cells that were infected by the subgroup B virus, presumably because they contained the tvb$^{s3}$ locus, were selected in media containing 300 µg/ml hygromycin B. This procedure gave rise to approximately 20 hygromycin B-resistant colonies. To provide fuirther support for the proposition that these cells contained tvb$^{s3}$, these cells were also challenged with 10$^4$ infectious units of another subgroup B-specific virus, RCASB-neo, which contained a gene that conferred resistance to growth in 300 µg/ml G418. A single primary transfectant was obtained (designated 11B), which was infected by both subgroup B viruses.

Southern blot analysis (Southern 1975) demonstrated that the primary transfectant contained approximately six independent RCASH-B proviruses. Since untransfected 3T3 cells are extremely resistant to infection by ALSV-B, the presence of multiple proviruses in this primary transfectant provided another indication that it expressed ALSV-B receptors. Additional Southern blot analysis, demonstrated that the primary transfectant contained approximately 20 copies each of B5/B6 chicken repeat DNA (Stumph W. E., et al. (1981) *Nuc. Acids Res.* 9:5383–97), and pMPHis plasmid DNA.

To segregate the putative tvb$^{s3}$ locus from irrelevant chicken DNA sequences in the primary transfectant, a second round of transfection and selection was performed. Primary transfectant DNA used for these experiments was prepared from cells infected by RCASH-B, but not by RCASB-neo. Approximately 2×10$^7$ mouse 3T3 cells were transfected with 200 µg of the primary transfectant DNA and 20 µg of plasmid pPur conferring resistance to puromycin. The secondary transfectants were selected in media containing 1 µg/ml puromycin, a protocol which gave rise to approximately 20,000 independent puromycin-resistant colonies. These cells were divided into three separate pools and challenged with 2×10$^7$ infectious units of the RCASB-neo virus. Cells infected by this virus were selected in media containing 300 µg/ml G418. This procedure generated a total of 48 G418-resistant colonies.

To obtain further evidence that these cells contained the putative tvb$^{s3}$ locus, these cells were also challenged with the subgroup B-specific RCASH-B virus, and infected cells were selected in media containing 300 µg/ml hygromycin B. This led to the isolation of 12 colonies from the three separate pools that had been infected by both subgroup B-viruses. These colonies displayed one of two phenotypes: four colonies were highly susceptible to RCASH-B, but the others were approximately 100-fold less susceptible. Importantly, cells derived from three transfectants that were highly susceptible to ALSV-B infection, were also approximately 100-fold more susceptible to infection by a virus (RCASH-D), containing the subgroup determining region of the subgroup D Schmidt-Ruppin viral strain and a gene conferring resistance to hygromycin B. This observation provided significant support for the idea that these cells contain tvb$^{s3}$.

In an attempt to identify the putative tvb$^{s3}$ locus in secondary transfectants that were susceptible to infection by ALSV-B and ALSV-D, Southern blot analysis (Southern 1975) was performed using genomic DNA prepared from these cells. These studies demonstrated that seven of the twelve clones contained the same copy of pMPHis plasmid DNA that had been used only in the first round of transfection. Because these seven clones were obtained from three separate pools of transfectants, they must have been derived from at least three independent secondary transfectants. The only possible explanation for this result is that this copy of plasmid DNA became tightly linked to the putative tvb$^{s3}$ locus when it was taken up by the primary transfectant, and that it frequently cosegregated with this gene during the second round of transfection. Subsequent Southern blot analysis of three of these clones (designated A15, B14, and C12), using radioactively-labeled probes derived from the plasmid DNA, demonstrated that these cells contained a shared region of transfected DNA, presumably tvb$^{s3}$.

The linked plasmid DNA sequences were used as a molecular tag to clone a fragment of the putative tvb$^{s3}$ locus. Briefly, genomic DNA from secondary transfectant C12 was digested with HindIII, and DNA fragments of approximately 6.5 to 8 kb were size-selected by agarose gel electrophoresis and subcloned into the λZAP vector (Stratagene). The genomic DNA library was screened using a radioactively-labeled DNA probe derived from the plasmid encoded histidinol-resistance gene. This led to the isolation of lambda clone BK-1c, containing the plasmid DNA and flanking genomic DNA sequences. Two restriction fragments derived from this clone, a 1.9 kb EcoRI-HindIII fragment and 1.5 kb EcoRI—EcoRI fragment, were then used to isolate an overlapping genomic clone, designated 1BK-9. Extensive Southern blot analysis, using radioactively-labeled restriction fragments of these two genomic clones as probes, revealed that the three transfectants C12, B14, A15, and other ALSV-B susceptible transfectants including A2 (which did not contain the linked plasmid DNA sequences), shared a region of transfected chicken genomic DNA, approximately 7.5 kb in length.

We postulated that if the shared locus encoded ALSV susceptibility factor(s), then the gene(s) responsible were most likely contained within the BK-9 genomic clone containing most of this locus. To test this idea, human 293 cells were transiently transfected with the BK-9 genomic DNA clone and were challenged with the RCASH-B virus, conferring resistance to hygromycin B. These studies demonstrated that the genomic DNA clone conferred susceptibility to ALSV-B infection.

The mRNA transcripts encoded by the functional λBK-9 genomic DNA clone were identified by northern blot analysis using polyadenylated RNA prepared from C/E CEFs and three radioactively-labeled DNA probes from the cloned locus (2.5 kb, 1.9 kb, and 1.5 kb, respectively). Each of these probes detected a similarly sized, approximately 2.5 kb, mRNA transcript. Because these probes spanned most of the shared region between the different transfectants, we hypothesized that this mRNA transcript might encode the putative ALSV-B susceptibility factor. To test this idea, a cDNA library was constructed from C/E CEFs using the λZAP express system (Stratagene). Briefly, this approach involved directional cloning of cDNA molecules between a CMV promoter and SV40 poly(A)/transcription-termination signals, in the pBK-CMV phagemid vector (Stratagene). The phagemid vector, a component of λZAP Express, also contains DNA sequences that direct DNA synthesis by a filamentous helper phage. This feature allowed production of plasmid products containing cDNA clones in the presence of ExAssist helper phage (Stratagene). This system was chosen because of the large numbers of recombinant cDNA clones that could be generated using the bacteriophage vector, and the ease of purifying these clones in plasmid-based mammalian expression vectors which could then immediately be used for functional studies.

The cDNA library was screened with each of the radioactively-labeled 2.5 kb, 1.9 kb, and 1.5 kb probes, and multiple clones were detected by cross-hybridization. These clones were isolated, subjected to the phagemid excision protocol to yield derivative plasmids, and the plasmids were transfected into human 293 cells and tested for their abilities to confer susceptibility to subgroup B viral entry. One clone, designated 7.6-2, encoded functional ALSV-B susceptibility factors in the 293 cells. This clone was subjected to DNA sequence analysis to identify its protein product. The functional cDNA clone encodes a Type I membrane protein with significant amino acid similarity to the Fas/TNFR protein superfamily. Specifically, the 127 amino acid long predicted extracellular domain contains two cysteine-rich motifs (FIG. 2) that are characteristic of different members of this family, which, as described above, include the TNFR, Fas, CD40, CD30, OX40, low affinity NGFR, CD27, 41BB (reviewed in Beutler B. and Van Huffel C. (1994) *Annals of the New York Academy of Sciences* 730:118–33) Based upon the spacing of cysteine residues, the first of these motifs in the putative Tvb protein appears to be most highly related to the second, instead of the first, motifs of human TNFR, hNGFR, and OX40. The second motif of the putative Tvb protein appears to be most highly related to the third motifs of Fas, the p75 TNFR, and CD40, with the most significant shared feature being an additional disulfide bond (Banner D W, et al. (1993) *Cell* 73:431–45), which in the putative Tvb protein is represented by Cys-88 and Cys-94 (SEQ ID No. 2, and FIG. 2).

Also, the cytoplasmic tail domain of the putative tvb protein contains a region with significant similarities to the defined "death domains" of the p55 TNFR and Fas (FIG. 3). Ligand-receptor interactions lead to clustering of these domains in the TNF receptor and in Fas, which in turn, signal cell-killing events either by necrosis or apoptosis. Indeed, these domains are also found in other proteins involved in signaling cell-death, including Reaper, TRADD, FADD and RIP (reviewed in Cleveland JL and Ihle JN (1995) *Cell* 81:479–82). Intriguingly, the putative Tvb protein has identical residues at five of the six positions revealed by alanine scanning mutagenesis to be important for cell killing events mediated by the human p55 TNFR. These residues include Leu-174, which is noteworthy because replacement of the corresponding residue (Ile-225) of murine Fas with Asn (the lpr mutation) leads to a major defect in apoptosis during lymphocyte development, resulting in a severe lymphoproliferative disorder (Nagata S. and Golstein P. (1995) *Science* 267:1449–56). The presence of a domain with the features of a "death domain" in the cytoplasmic region of the putative Tvb protein raises the interesting possibility that interaction of this protein with subgroup B and subgroup D Env-glycoproteins might contribute to the cell-killing events associated with infection of cells by ALSV-B and ALSV-D.

To facilitate studies of the binding between the putative tvb protein and the subgroup B SU Env protein, two different subgroup B-specific SU-immunoadhesins (SUB-rIgG and SUB-mIgG) were generated These fusion proteins comprise the SU portion of a subgroup B SU protein fused to the constant region of rabbit (rIgG) and mouse (mIgG) immunoglobulins. The resultant proteins were used like antibodies for binding studies by immunoprecipitation, immunoblotting, and FACS analyses. The SUB-rIgG and SUB-mIgG proteins specifically immunoprecipitated three proteins of approximately 47 kD, 44 kD, and 41 kD, from transfected human 293 cells expressing the putative tvb protein. These proteins were not precipitated by two control immunoadhesins, SUA-rIgG which comprises the subgroup A-specific ALV SU Env protein fused in frame with the Fc portion of rabbit IgG, and tva-rIgG comprising the subgroup A-ALV receptor fused to rabbit IgG. Furthermore, these three proteins were not precipitated by the subgroup B SU-immunoadhesins from either non-transfected human 293 cells or from transfected human 293 cells expressing the subgroup A viral receptor, tva. Other experiments have demonstrated that incubating these three proteins with endoglycosidase H to remove sugar residues, results in the generation of only one protein which migrates at 41 kD. Therefore, these results demonstrate that the subgroup B SU-immunoadhesins specifically immunoprecipitate the candidate tvb proteins which are either non-glycosylated, glycosylated at one of the two putative N-linked glycosylation sites (Asn-54 or Asn-105), or glycosylated at both of these sites. This specific binding activity is consistent with identifying the putative tvb protein as a subgroup B-specific viral receptor. Indeed, other FACS experiments have demonstrated specific binding between the subgroup B SU-immunoadhesins and transfected human 293 cells expressing the putative tvb protein.

Figure 4:
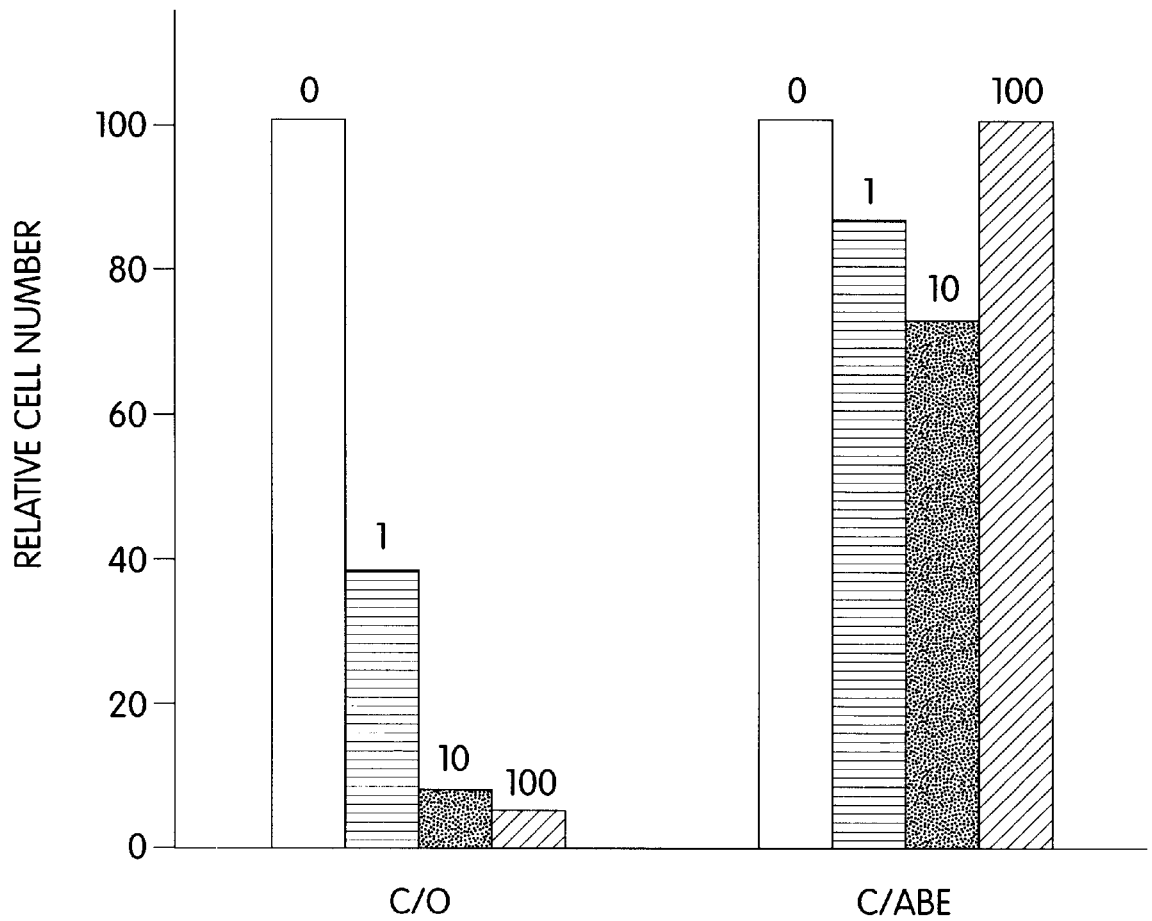
FIG. 4 is a graph illustrating that chicken cells genetically-resistant to subgroup B viral infection do not exhibit cytopathic effects.

As demonstrated in FIG. 4, chicken cells genetically-resistant to subgroup B viral infection do not exhibit cytopathic effects. Briefly, chicken embryo fibroblasts that were susceptible (C/O) or resistant (C/ABE) to subgroup B viral infection were plated in 24-well plates and incubated with either 1, 10, or 100 µl aliquots of crude extracellular supernatants containing the SUB-Immunuoadhesin, or no immunoadhesin, and 7.5 mg/ml cycloheximide. After 4 days the cells were split and incubated for a further 5 days with the same amounts of SUB-immunoadhesin and cycloheximide. The adherent cells were then trypsinized and counted using a hemacytometer. The graph shows the relative numbers for each cell population. The enhanced cell-killing of the C/O cells by the immunoadhesin, which is manifested as accelerated cell death in the presence of cycloheximide, was specific for subgroup B SU. This accelerated cell death was not observed with cells incubated with a control subgroup A SU-immunoadhesin (data not shown). Also, in other experiments we have demonstrated that the accelerated killing is most likely due to apoptosis because the dead cells contain the characteristic nucleosomal DNA ladders that result from programmed cell death.

FIG. 5 demonstrates that the putative tvb protein confers susceptibility to ALV-B infection and increases susceptibility to infection by mammal-tropic ALV-D. Monkey COS-7 cells were transfected by the calcium phosphate method (Wigler M., et al. (1977) *Cell* 11:223–32) with 10 micrograms of the plasmid p7.6#2 encoding the candidate tvb protein. After 48 hours, the cells were split onto 6-well plates and challenged with Subgroup A, B, C and D RCAS viral vectors containing the G418-resistance gene under the control of the HSV thymidine kinase promoter. After 24 hours, infected cells were selected in media containing 600 µg/ml G418 and the resistant cells were counted after 14 days.

Methods

Human 293 cells were plated at approximately 20% confluence on 100 mm tissue culture plates in Dulbecco's Modified Eagles Media containing 10% bovine calf serum (DMEM-10% FCS). The cells were transfected by the calcium phosphate method (Wigler, supra) with either no DNA, 15 μg of plasmid p7.6#2 encoding the putative tvb protein, and 15 μg of plasmid pKZ261 encoding the tva protein. The cells were incubated with the calcium phosphate precipitates for 18 hours and the media was then replaced with DMEM-10% FCS. After a 22 hour incubation, the cells were metabolically-labeled with $^{35}$-S-cysteine (ICN chemicals). Briefly, the cells were incubated for one hour in cysteine and methionine-free DMEM containing 1% dialyzed fetal calf serum, and then in the same media were supplemented with 100 μCi/ml $^{35}$S-cysteine for 2 hours. The cells were then washed once with ice-cold phosphate buffered saline and lysed in 1 ml NP-40 lysis buffer containing aprotinin and PMSF. The nuclei were then pelleted in a microfuge at 4° C. for 5 minutes. 100 μl fractions of each of the supernatants were then incubated at 4° C. for 45 minutes with 400 μl NP-40 lysis buffer and 40 μl of protein A-sepharose bead mixture that had been previously preincubated with 1ml of extracellular supernatants containing either SUA-rIgG, SUB-rIgG, SUB-mIgG, or tva-rIgG immunoadhesins. The protein A-sepharose beads comprise 5 μl protein A-sepharose CL-4B (Sigma), 15 μl of sepharose CL-4B (Sigma) and 20 μl NP-40 lysis buffer. Following the incubation, the beads were pelleted in a microfuge and washed 3 times each with 1 ml of NP-40 lysis buffer and then the bound proteins were prepared for SDS-PAGE by boiling in 50 μl Laemmli-gel loading buffer. 12.5 μl fractions of each sample were then subjected to electrophoresis on a 10% SDS-polyacrylamide gel, the gel was dried and exposed to Kodak XAR-5 film.

Preparation of the immunoadhesins-containing extracellular supernatants

Human 293 cells were plated at 20% confluence on 150 mm tissue culture plates in DMEM-10% FCS. The plates were transfected for 18 to 19 hours by the calcium phosphate method (Wigler, supra) with 45 μg of either plasmid pKZ387 (encoding SUA-rIgG); plasmid pKZ452 (encoding SUB-rIgG); plasmid pKZ453 (encoding SUB-mIgG); plasmid pKZ457 (encoding tva-rIgG). The plates were rinsed with 4 to 5 ml of phosphate buffered saline and incubated with 20 ml of DMEM-10% FCS, which was previously precleared of bovine immunoglobulins by passing three times over a protein A-column (Pharmacia Hi-Trap). The media was collected from the cells after a 24 hour incubation and replaced with another 20 ml aliquot of the precleared DMEM-10% FCS. The second aliquot of media was harvested after another 24 hour incubation and the collected media was pooled, filtered through a 0.45 μm filter and stored at −20° C. The media was thawed prior to its use above.

All of the above-cited references and publications are hereby incorporated by reference.

What is claimed is:

1. An isolated nucleic acid which specifically hybridizes under highly stringent wash conditions having a salt concentration of about 0.2×SSC at 50° C. to the nucleotide sequence of SEQ ID NO: 1 or a sequence complementary thereto, and encodes a tumor virus b susceptibility (tvb) polypeptide characterized by one or more of (i) an extracellular ligand binding domain having two cysteine rich domains, (ii) a transmembrane domain, and (iii) a cytoplasmic domain including a death domain, wherein said polypeptide binds a retrovirus.

2. The nucleic acid of claim 1, which tvb polypeptide specifically binds to an avian leukosis/sarcoma virus.

3. The nucleic acid of claim 1, which tvb polypeptide has a core molecular weight of 39–49 kilodaltons.

4. The isolated nucleic acid of claim 1 which encodes a tvb polypeptide having an extracellular ligand binding domain having two cysteine rich domains, wherein the cysteine rich domains correspond to the amino acid sequences Cys59–Cys101 and Cys103–Cys143 of SEQ ID NO: 2, respectively.

5. The isolated nucleic acid of claim 1 which encodes a tvb polypeptide having a death domain, wherein the death domain corresponds to the amino acid sequence Val281-Ser355 of SEQ ID NO: 2.

6. The nucleic acid of claim 1, wherein the tvb polypeptide is a fusion protein further comprising a second polypeptide sequence having an amino acid sequence unrelated to a tvb polypeptide sequence.

7. The nucleic acid of claim 6, wherein the fusion protein includes, as a second polypeptide sequence, a polypeptide which functions as a detectable label for detecting the presence of the fusion protein or as a matrix-binding domain for immobilizing the fusion protein.

8. The nucleic acid of claim 1, further comprising a transcriptional regulatory sequence operably linked to the tvb-encoding nucleotide sequence so as to render the nucleic acid suitable for use as an expression vector.

9. An expression vector, capable of replicating in at least one of a prokaryotic cell and eukaryotic cell, comprising the nucleic acid of claim 8.

10. A host cell transfected with the expression vector of claim 9 and expressing the tvb polypeptide.

11. A method of producing a recombinant tvb polypeptide comprising culturing the cell of claim 10 in a cell culture medium to express a recombinant tvb polypeptide and isolating the recombinant tvb polypeptide from the cell culture.

12. A test kit for detecting cells which contain a tvb mRNA transcript, comprising the nucleic acid of claim 1 for measuring, in the sample of cells, a level of nucleic acid encoding a tvb protein, and a diluent.

13. The nucleic acid of claim 1, wherein said polypeptide comprises the ligand binding domain and lacks the transmembrane domain and the cytoplasmic domains.

14. The nucleic acid of claim 1, wherein said polypeptide binds to an avian leukosis/sarcoma virus (ALSV) selected from the group consisting of ALSV-B and ALSV-D subtypes.

15. A recombinant expression system, comprising
(a) a gene construct including an isolated nucleic acid which specifically hybridizes under highly stringent wash conditions having a salt concentration of about 0.2×SSC at 50° C. to the nucleotide sequence of SEQ ID No. 1 or a sequence complementary thereto, and encodes a tumor virus b susceptibility (tvb) polypeptide characterized by one or more of (i) an extracellular ligand binding domain having two cysteine rich domains, (ii) a transmembrane domain, and (iii) a cytoplasmic domain including a death domain, wherein said polypeptide binds a retrovirus, said gene construct being operably linked to a transcriptional regulatory sequence for causing expression of the tvb polypeptide in eukaryotic cells.

16. An isolated nucleic acid molecule comprising the nucleotide sequence of SEQ ID NO:1.

17. An isolated nucleic acid molecule comprising a nucleotide sequence encoding a protein which comprises an amino acid sequence of SEQ ID NO:2.

* * * * *

UNITED STATES PATENT AND TRADEMARK OFFICE
CERTIFICATE OF CORRECTION

PATENT NO. : 5,912,141
DATED : June 15, 1999
INVENTOR(S) : Jürgen Brojatsch *et al.*

It is certified that error appears in the above-identified patent and that said Letters Patent is hereby corrected as shown below:

Please insert the following at the Title section, [54], at Page 1:

--NUCLEIC ACIDS ENCODING TUMOR VIRUS B SUSCEPTIBILITY GENES--

Signed and Sealed this

Second Day of November, 1999

*Attest:*

Q. TODD DICKINSON

*Attesting Offic

UNITED STATES PATENT AND TRADEMARK OFFICE
CERTIFICATE OF CORRECTION

PATENT NO. : 5,912,141
DATED : June 15, 1999
INVENTOR(S) : Jürgen Brojatsch et al.

It is certified that error appears in the above-identified patent and that said Letters Patent is hereby corrected as shown below:

Column 1, line 3 please insert:

--Government Funding

The work described herein was supported in part by the following grant from the National Institutes of Health: CA62000--

Signed and Sealed this

Twenty-first Day of December, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,912,141
APPLICATION NO. : 08/651579
DATED : June 15, 1999
INVENTOR(S) : Brojatsch et al.

Page 1 of 1

It is certified that error appears in the above-identified patent and that said Letters Patent is hereby corrected as shown below:

In the Specification

At Column 1, Line number 3, please add the following:
GOVERNMENT SUPPORT
This invention was made with government support under CA062000 awarded by the National Institutes of Health. The government has certain rights in the invention.

This certificate supersedes the Certificate of Correction issued December 21, 1999.

Signed and Sealed this
Nineteenth Day of August, 2025

Coke Morgan Stewart
*Acting Director of the United States Patent and Trademark Office*